(12) United States Patent
Krestel et al.

(10) Patent No.: US 10,519,178 B2
(45) Date of Patent: Dec. 31, 2019

(54) BI-NUCLEAR MAIN GROUP METAL PHOSPHORESCENT EMITTER

(71) Applicant: Siemens Aktiengesellschaft, Munich (DE)

(72) Inventors: Ana-Maria Krestel, Erlangen (DE); Anna Maltenberger, Leutenbach (DE); Marina A Petrukhina, Schenectady, NY (US); Guenter Schmid, Hemhofen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 207 days.

(21) Appl. No.: 15/314,256

(22) PCT Filed: Apr. 24, 2015

(86) PCT No.: PCT/EP2015/058917
§ 371 (c)(1),
(2) Date: Nov. 28, 2016

(87) PCT Pub. No.: WO2015/180901
PCT Pub. Date: Dec. 3, 2015

(65) Prior Publication Data
US 2018/0240975 A1 Aug. 23, 2018

Related U.S. Application Data

(60) Provisional application No. 62/004,486, filed on May 29, 2014.

(51) Int. Cl.
| | | |
|---|---|---|
| *C07F 9/94* | (2006.01) | |
| *H01L 51/00* | (2006.01) | |
| *C09K 11/06* | (2006.01) | |
| *C07F 15/00* | (2006.01) | |
| *H01L 51/50* | (2006.01) | |

(52) U.S. Cl.
CPC ............ *C07F 9/94* (2013.01); *C07F 15/0033* (2013.01); *C09K 11/06* (2013.01); *H01L 51/009* (2013.01); *C09K 2211/1007* (2013.01); *C09K 2211/1029* (2013.01); *C09K 2211/1044* (2013.01); *C09K 2211/188* (2013.01); *H01L 51/5016* (2013.01); *Y02E 10/52* (2013.01); *Y02E 10/549* (2013.01)

(58) Field of Classification Search
CPC ...................................................... C07F 9/94
See application file for complete search history.

(56) References Cited

U.S. PATENT DOCUMENTS

2008/0015356 A1  1/2008  Kakuta et al. ............... 546/10
2013/0324733 A1  12/2013  Fujimura et al. ............. 346/4

FOREIGN PATENT DOCUMENTS

| DE | 10360681 A1 | 7/2005 | ............. C09K 11/06 |
| WO | 2012/016074 A1 | 2/2012 | ............. B05D 7/24 |
| WO | 2015/180901 A1 | 12/2015 | ............. C09K 11/06 |

OTHER PUBLICATIONS

Harrowfield et al. CAS Accession No. 1996:749707.*
Omary, Mohammad A. et al., "Enhancement of the Phosphorescence of Organic Luminophores upon Interaction with a Mercury Trifunctional Lewis Acid," Inorganic Chemistry, vol. 42, pp. 2176-2178, Jan. 21, 2003.
Gao, Junli et al., "Di-µ-benzoato-K³ O,O':O;K³O:O,O'-bis [(acetato-$_K$O)(1, 10-phenanthroline-K²N,N)lead(II)] dehydrate," ACTA Crystallographica Section E Structure vol. 219, No. 8, 13 pages, 2009.
International Search Report and Written Opinion, Application No. PCT/EP2015/058917, 11 pages, dated Aug. 12, 2015.
Stavila, Vitalie et al., "Synthesis and Characterization of New Phenylbis(salicylato)bismuth(III) Complexes," Organometallics, vol. 26, No. 14, pp. 3321-3328, Feb. 5, 2007.
Yang, Shuping et al., "Synthesis, Crystal Structure and Antibacterial Activity of A Bismuth (III) Complex [Bi2(PPA)6•(Phen)2] with Phenylacetic Acid and 1,10-Phenanthroline," Journal of Chemistry, vol. 70, No. 4, pp. 519-524 (Chinese w/ English abstract), Dec. 19, 2011.
Gao, Junli, "Crystalline Structure and Property of O-Phenanthroline and its Derivative Metal Complex," China Excellent Master's Dissertation Database, No. 2, 11 pages (Chinese w/ English translation), 2012.
Sun, Xuejian, "Synthesis, Characterization and Optoelectronic Properties of a Metal Complex Containing S/N Ligand", China Excellent Master's Dissertation Database, No. 6, 11 pages (Chinese w/ English translation), 2012.

(Continued)

*Primary Examiner* — Joseph R Kosack
(74) *Attorney, Agent, or Firm* — Slayden Grubert Beard PLLC

(57) ABSTRACT

A bi-nuclear phosphorescent emitter according to the following formula is disclosed. The emitter may include metal atoms $M_1$ and $M_2$, fluorescent emitter ligands $L_F$, $L_F'$, terminal ligands $L_T$, $L_T'$, and bridging ligands $L_V$, $L_V'$, wherein $M_1$ and $M_2$ are In, Tl, Sn, Pb, Sb, and Bi; $L_F$ and $L_F'$ are comprise substituted or non-substituted C6-C70 aromatics or heteroaromatics; $L_V$ and $L_V'$ are fluorinated or non-fluorinated, bi-dentate C2-C30 heteroalkyl or heteroaromatics; $L_T$ and $L_T'$ are fluorinated or non-fluorinated, mono-, bi-, or tri-dentate C2-C30 O—, S—, N, heteroalkyl or heteroaromatics; and n and m are 1 or 2 independently of one another.

12 Claims, 4 Drawing Sheets

(56) References Cited

OTHER PUBLICATIONS

Jin, Juan et al., "New Photoluminescence Acylhydrazidate-Coordinated Complexes," Dalton Transactions, The Royal Society of Chemistry, vol. 41, pp. 2382-2392, 2012.
Chinese Office Action, Application No. 201580028360.5, 26 pages, dated Mar. 5, 2018.
Korean Office Action, Application No. 2018018805417, 12 pages, dated Mar. 15, 2018.

* cited by examiner

BI-NUCLEAR MAIN GROUP METAL PHOSPHORESCENT EMITTER

CROSS-REFERENCE TO RELATED APPLICATIONS

This application is a U.S. National Stage Application of International Application No. PCT/EP2015/058917 filed Apr. 24, 2015, which designates the United States of America, and claims priority to U.S. Provisional Application No. 62/004,486 filed May 29, 2014, the contents of which are hereby incorporated by reference in their entirety.

TECHNICAL FIELD

The present invention relates to a bi-nuclear phosphorescent emitter according to formula I

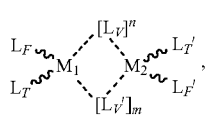

formula I wherein the emitter comprises metal atoms $M_1$ and $M_2$, fluorescent emitter ligands $L_F$, $L_F'$, terminal ligands $L_T$, $L_T'$, and bridging ligands $L_V$, $L_V'$, wherein
$M_1$ and $M_2$ are chosen independently of one another from the group of heavy main group metals comprising In, Tl, Sn, Pb, Sb, and Bi;
$L_F$, $L_F'$ are chosen independently of one another from the group comprising substituted or non-substituted C6-C70 aromatics or heteroaromatics;
$L_V$, $L_V'$ are chosen independently of one another from the group comprising fluorinated or non-fluorinated, bi-dentate C2-C30 heteroalkyl or heteroaromatics;
$L_T$, $L_T'$ are chosen independently of one another from the group comprising fluorinated or non-fluorinated, mono-, bi-, or tri-dentate C2-C30 O—, S—, N—, heteroalkyl or heteroaromatics; n, m are 1 or 2 independently of one another.

BACKGROUND

The light-emitting systems in organic electronics may fundamentally be classified in two different groups. On the one hand, the longer known and commercially available systems, which are capable, utilizing fluorescence properties of organic or organic/inorganic complexes, of converting electrical energy into light. On the other hand, systems, the conversion properties of which are based on electronic transitions, which can be associated with phosphorescence. The latter are at least theoretically capable, in consideration of the applicable quantum statistics, of reaching an internal quantum efficiency of 100%. This is in contrast to solely fluorescent emitters, which can have a maximum internal quantum yield of only 25% because of the quantum statistics.

A previously followed approach was to use metal complexes having metals of the sixth period as the emission or absorption centers. Phosphorescence also does occur in conjunction with the elements of the fourth and fifth periods of the periodic system, but the complexes of the metals of the sixth period have proven themselves. Depending on the location of the elements in this period, the origin of the phosphorescence is weighted differently within the orbital structure of the complexes in this case.

In the lanthanides, both the HOMO (highest occupied molecular orbital) and also the LUMO (lowest unoccupied molecular orbital) are predominantly metal-centered, i.e., the component of the ligand orbitals is relatively weakly pronounced. As a result, the emission wavelength (color) of the emitters is established almost exclusively by the band structure of the metal (examples europium=red, terbium=green). Because of the strong shielding of the f electrons of these metals, ligands coupled to the metal are capable of splitting the energies of the $f^n$ configuration of the metals only around approximately 100 cm$^{-1}$, so that the spectroscopy due to their ligand field significantly differentiates the d ions from that of the f ions. In ions of the lanthanides, the color results from transitions of f into unoccupied s, p, and d orbitals.

If one travels along the period to the elements osmium, iridium, platinum, and gold, ligand fields thus split the metal orbitals by a factor of 10-100 times more than in the case of the lanthanides. Therefore, by variation of the ligands, practically the entire visible wavelength spectrum may be represented using these elements. Due to the strong coupling of the orbital angular momentum of the metal atom to the spin angular momentum of the electrons, phosphorescence is obtained in the emitters. The HOMO is usually metal-centered in this case, while the LUMO is usually ligand-centered. The radiant transitions are therefore referred to as metal-ligand charge transfer transitions (MLCT).

Both OLEDs (organic light-emitting diodes) and also OLEECs (organic light-emitting electrochemical cells) presently use almost exclusively iridium complexes as phosphorescent emitters. In the case of OLEDs, the emitter complexes are uncharged; in the case of OLEECs, ionic, i.e., charged emitter complexes are used. The use of iridium in these components has a severe disadvantage, however. The yearly production of iridium is well below 10 tons (3 tons in 2000). This has the result that the material costs provide a significant contribution to the production costs of organic electrical components. In addition, iridium emitters are not capable of efficiently imaging the entire spectrum of visible light. Thus, stable blue iridium emitters are rather rare, for example, which opposes a flexible use of these materials in OLED or OLEEC applications.

In more recent literature, in contrast, there are some approaches which propose "triplet harvesting" also using emitters which are not based on iridium. Thus, for example, Omary et al. in "Enhancement of the Phosphorescence of Organic Luminophores upon Interaction with a Mercury Trifunctional Lewis Acid" (Mohammad A. Omary, Refaie M. Kassab, Mason R. Haneline, O. Elbjeirami, and Francois P. Gabbai, Inorg. Chem. 2003, 42, 2176-2178) refer to the possibility of achieving sufficient phosphorescence of solely organic emitters by way of the use of mercury. Due to the heavy atom effect of mercury in a matrix made of organic ligands, a singlet-triplet/triplet-singlet transition of the excited electrons of the organic matrix is enabled in quantum mechanics (ISC, inter-system crossing), which results in a significant reduction of the lifetime of the excited electronic (triplet) states and avoids undesired saturation of the occupation of said states. The cause of this mechanism is the spin-orbit coupling of the mercury heavy atom to the excited electrons of the organic matrix. In contrast, it is disadvantageous that the use of mercury is problematic as a result of toxic and environmental-political aspects.

WO 2012/016074 A1, in contrast, describes a thin layer comprising a compound of the formula

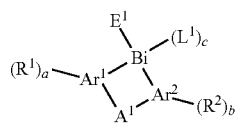

wherein $Ar^1$ and $Ar^2$ are each independently a C3-30 aromatic ring; $R^1$ and $R^2$ are a substituent; a and b are each independently an integer from 0 to 12, wherein, if a is 2 or more, each residue $R^1$ is optionally different from one another, and two residues $R^1$ are optionally bonded to one another to form a ring structure, and, if b is 2 or more, each residue $R^2$ is optionally different from one another and two residues $R^2$ are optionally bonded to one another to form a ring structure; $A^1$ is any type of a direct bond, —O—, —S—, —S(=O)—, —S(=O)$_2$—, —PR$^3$—, —NR$^4$—, and —C(R$^5$)$_2$—; $R^3$ is a hydrogen atom or a substituent; $R^4$ is a hydrogen atom or a substituent; $R^5$ is a hydrogen atom or a substituent and two residues $R^5$ are optionally different from one another; $E^1$ is a monovalent residue having 50 or fewer carbon atoms; $L^1$ is a ligand having 50 or fewer carbon atoms; c is an integer from 0 to 3, wherein, if c is 2 or more, each residue $L^1$ is optionally different from one another; and each combination of a combination of $E^1$ and $Ar^1$ and a combination of $E^1$ and $Ar^2$ optionally forms a bond; and, if c is 1 to 3, each combination of a combination of $L^1$ and $E^1$, a combination of $L^1$ and $Ar^1$, a combination of $L^1$ and $Ar^2$, and a combination of $L^1$ and $L^1$ optionally forms a bond. In contrast, it is disadvantageous that the described compounds only have an inadequate quantum yield and are not sufficiently stable in solution, so that they decompose.

DE 103 60 681 A1 discloses main group metal-diketonato complexes according to the following formula

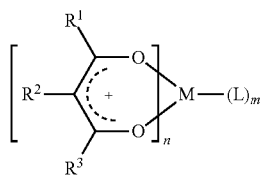

as phosphorescent emitter molecules in organic light-emitting diodes (OLEDs), wherein M can be Tl(I), Pb(II), and Bi(III). Furthermore, the use of these main group metal-diketonato complexes as light-emitting layers in OLEDs, light-emitting layers containing at least one main group metal-diketonato complex, an OLED containing this light-emitting layer, and devices which contain an OLED according to the invention are disclosed. In contrast, it was possible to show in experiments that the above-mentioned compounds, which are synthesized under strict water exclusion, do not display emission based on phosphorescence after electronic excitation. It is highly probable that the described phosphorescent emissions originate from oxo clusters which are not definable in greater detail, and which have formed in an uncontrolled manner, for example, by hydrolysis in the scope of the production. This special solution has the disadvantage that the n-system of these acetyl acetonate ligands, in particular the described fully fluorinated variants, is less pronounced and only permits low phosphorescence yields as the sole phosphorescent emitter.

SUMMARY

One embodiment provides a bi-nuclear phosphorescent emitter according to formula I

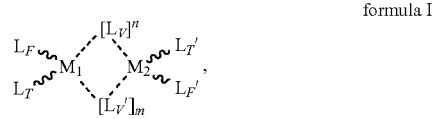

formula I wherein the emitter comprises metal atoms $M_1$ and $M_2$, fluorescent emitter ligands $L_F$, $L_F'$, terminal ligands $L_T$, $L_T'$, and bridging ligands $L_V$, $L_V'$, wherein $M_1$ and $M_2$ are chosen independently of one another from the group of heavy main group metals comprising In, Tl, Sn, Pb, Sb, and Bi;

$L_F$, $L_F'$ are chosen independently of one another from the group comprising substituted or non-substituted C6-C70 aromatics or heteroaromatics;

$L_V$, $L_V'$ are chosen independently of one another from the group comprising fluorinated or non-fluorinated, bi-dentate C2-C30 heteroalkyl or heteroaromatics; $L_T$, $L_T'$ are chosen independently of one another from the group comprising fluorinated or non-fluorinated, mono-, bi-, or tri-dentate C2-C30 O—, S—, N—, heteroalkyl or heteroaromatics;

n, m are 1 or 2 independently of one another.

In one embodiment, $M_1$ and $M_2$ are chosen independently of one another from the group comprising Sb, As, and Bi and n, m=2.

In one embodiment, $M_1$ and $M_2$ are chosen independently of one another from the group comprising Pb and Sn and n, m=1 or 2.

In one embodiment, the emitter is a homonuclear emitter with $M_1$=$M_2$=Bi.

In one embodiment, the distances between at least one metal atom and the ligands $L_V$, $L_V'$, $L_T$, $L_T'$ coordinated thereon are greater than or equal to 2.2 Å and less than or equal to 3.0 Å.

In one embodiment, at least one of $L_F$, $L_F'$ is chosen from the group comprising substituted or non-substituted mono-, di-, or tri-dentate C6-C70 N-heteroaromatics.

In one embodiment, at least one of $L_F$, $L_F'$ is chosen from the group comprising substituted or non-substituted C6-C70 2,2'-bipyridines.

In one embodiment, at least one of $L_F$, $L_F'$ is chosen from the group comprising substituted or non-substituted mono-, di-, or tri-dentate C6-C70 N-heteroaromatics comprising at least one carbazole unit.

In one embodiment, at least one of $L_F$, $L_F'$ is chosen from the group comprising 4,7-di(9H-carbazol-9-yl)-1,10-phenanthroline, 2,6-bis(3-(9H-carbazol-9-yl)phenyl)pyridine, and 3,5-bis(3-(9H-carbazol-9-yl)phenyl)pyridine.

In one embodiment, at least one of $L_V$, $L_V'$ is chosen from the group comprising fluorinated or non-fluorinated C2-C30 O—, S—, N—, heteroalkyl, heterocycloalkyl, or heteroaromatics.

In one embodiment, the emitter corresponds to following formula II, formula II

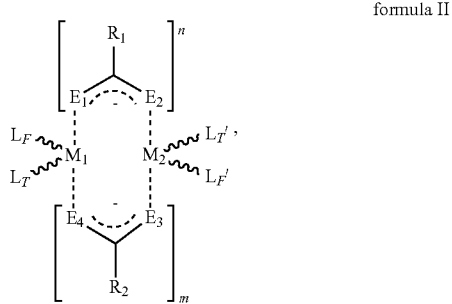

wherein
$R_1$, $R_2$ are chosen independently of one another from the group comprising fluorinated or non-fluorinated C1-C30 alkyl, cycloalkyl, aryl, heteroalkyl, heterocycloalkyl, heteroaryl; $E_1$, $E_2$, $E_3$, $E_4$ are chosen independently of one another from the group comprising O, S, NR, wherein R=H, D.

In one embodiment, at least one of the ligands $L_V$, $L_V'$ is chosen from the group comprising fluorinated or non-fluorinated aliphatic or aromatic C2-C30 carboxylates.

In one embodiment, at least one of the ligands $L_V$, $L_V'$ is chosen from the group comprising C2-C30 acetate, fluoroacetate, fluorobenzoate, fluoromethylbenzoate, fluoromethyl fluorobenzoate, di-fluoromethyl-benzoate, di-fluoromethyl-fluorobenzoate.

In one embodiment, at least one of the ligands $L_T$, $L_T'$ is chosen from the group comprising fluorinated or non-fluorinated aliphatic or aromatic C2-C30 alcoholates, carboxylates, benzoates, or acetylacetonates.

In one embodiment, at least one of the ligands $L_T$, $L_T'$ is chosen from the group comprising C2-C30 acetate, fluoroacetate, fluorobenzoate, fluoromethylbenzoate, fluoromethylfluorobenzoate, di-fluoromethyl-benzoate, di-fluoromethyl-fluorobenzoate.

In one embodiment, each of the ligands $L_V$, $L_V'$, $L_T$, $L_T'$ is chosen from the group comprising C2-C30 acetate, fluoroacetate, fluorobenzoate, fluoromethylbenzoate, fluoromethylfluorobenzoate, di-fluoromethyl-benzoate, di-fluoromethyl-fluorobenzoate.

Another embodiment provides a method for producing organic electric layers having organic emitters which are phosphorescent at room temperature, wherein organic phosphorescent emitters as disclosed herein are provided within a layer on a substrate.

Another embodiment provides an organic electric layer produced according to a method as disclosed above.

Another embodiment provides for the use of a layer as disclosed above as an active layer in an organic electric component for converting electric current into light or light into electric current or light into light of another wavelength.

Another embodiment provides an organic semiconductor component selected from the group comprising photodiodes, solar cells, organic light-emitting diodes, light-emitting electrochemical cells, containing a phosphorescent emitter as disclosed above.

BRIEF DESCRIPTION OF THE DRAWINGS

Example aspects and embodiments of the above-described organic semiconductor components, emitters, layer, and method are discussed in detail below with reference to the figures, in which.

DETAILED DESCRIPTION

Figure 1:
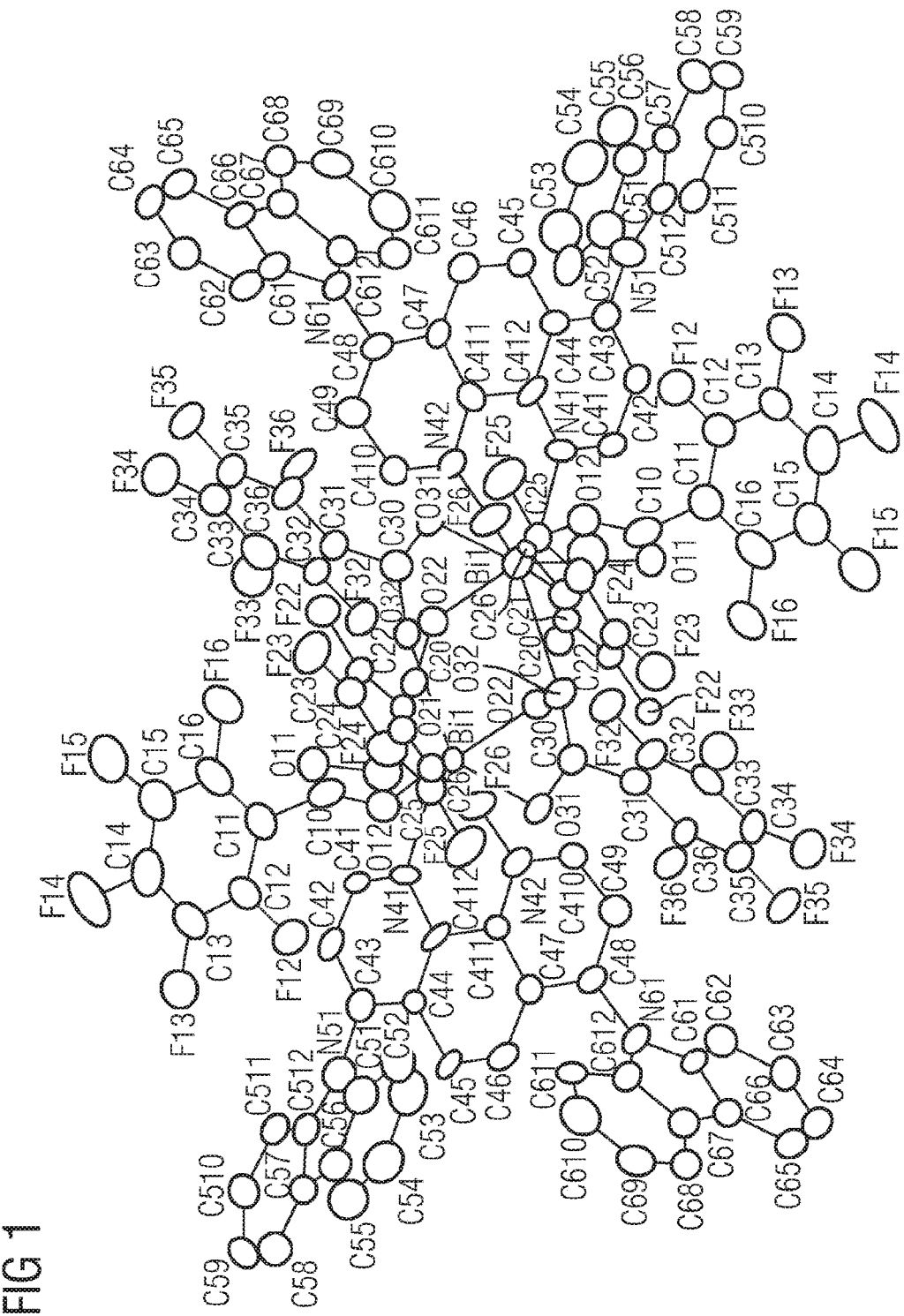
FIG. 1 shows a structure of a bi-nuclear phosphorescent emitter according to an embodiment having the composition hexakis-(µ-pentafluorobenzoato-k2O:O')bis[(4,7-di(9H-carbazol-9-yl)-1,10-phenanthroline-k2 N:N')bismuth(III)] looking toward the BUPH1 ligands coordinated on a bismuth atom (complex (1))

Embodiments of the present invention provide novel phosphorescent emitters, which are highly efficient, environmentally compatible, and available and are adaptable in their chromatic properties. Other embodiments provide a method, using which layers of such phosphorescent emitters are obtainable, and also components which contain these phosphorescent emitters according to the invention.

Some embodiments provide a bi-nuclear phosphorescent emitter according to formula I

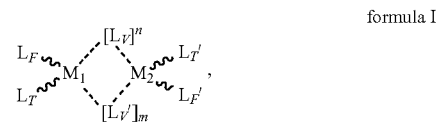

formula I is wherein the emitter comprises metal atoms $M_1$ and $M_2$, fluorescent emitter ligands $L_F$, $L_F'$, terminal ligands $L_T$, $L_T'$, and bridging ligands $L_V$, $L_V'$, wherein $M_1$ and $M_2$ are chosen independently of one another from the group of heavy main group metals comprising In, Tl, Sn, Pb, Sb, and Bi; $L_F$, $L_F'$ are chosen independently of one another from the group comprising substituted or non-substituted C6-C70 aromatics or heteroaromatics; $L_V$, $L_V'$ are chosen independently of one another from the group comprising fluorinated or non-fluorinated, bi-dentate C2-C30 heteroalkyl or heteroaromatics; $L_T$, $L_T'$ are chosen independently of one another from the group comprising fluorinated or non-fluorinated, mono-, bi-, or tri-dentate C2-C30 O—, S—, N—, heteroalkyl or heteroaromatics; n, m are 1 or 2 independently of one another. It has been shown that this form of bi-nuclear emitter may be produced easily and cost-effectively and displays a high quantum yield. Thus, inter alia, layers may also be obtained which display high luminance, rapid response behavior, and good long-term stability. In this case, in particular the bi-nuclear emitters which have two heavy main group metals appear to be capable of opening the phosphorescence channels of the organic emitter ligands particularly effectively. Without being bound by the theory, this could be because of the special steric construction of the entire emitter, which enables particularly effective spin-orbit coupling of the heavy metal atoms to the emitter ligands. In addition, it cannot be precluded that a certain interaction exists between the two metal centers, which has a favorable effect on the phosphorescence properties of the entire complex, i.e., in particular the organic emitters here. Furthermore, it is advantageously possible to influence the chromatic properties of the entire complex by the selection of the bridging and terminal ligands. Because of the fact that the phosphorescence is only induced by the organic emitters, by way of modification of the ligands, in particular the n-system thereof, the emission wavelength of the emitters can furthermore be tuned. It is possible in particular to synthesize heteroleptic complexes or accumulation compounds, which enable emissions via the orbitals of differently constructed ligands/emitters. This additionally increases the variety for producing the organic phosphorescent emitters according to the invention. Because of the bridging of the two metal centers via at least two bridging ligands, in addition, particularly stable complexes can result, which have little tendency toward further crystallization and can therefore be particularly long-lived. This can contribute to longer durability of layers having these phosphorescent emitters or electronic components containing these layers.

A bi-nuclear phosphorescent emitter in the meaning of the invention is a two-core complex, in which the two cores are formed by heavy main group metals. The two cores are connected in this case by at least two or also more ligands, which are each coordinated on the two cores. These are the bridging ligands $L_V$. A direct metal-metal bond can exist between these two cores, but does not have to. Furthermore, the emitter also has ligands which are each only coordinated on one of the metal cores. These are the terminal ligands $L_T$ and the fluorescent emitters $L_F$. The type of the coordination of the ligands is not restricted in this case to a σ-bond, but can also result due to n-bonds, or also in general by Coulomb interactions. The individual ligands can themselves be provided as electrically neutral or charged in this case. The emission occurs in this case essentially due to the organic ligands, the metal atoms provide essentially no contribution to the phosphorescence, they only provide their orbital angular momentum. The proportion of the phosphorescent emission of the complex induced by electronic inter-ligand and intra-ligand transitions under solely electronic excitation can be greater than or equal to 25% and less than or equal to 100% in relation to the total emission in this case. The coordination of the fluorescent emitters on the coordination sphere of the bi-nuclear complex can open an effective "phosphorescence channel" of the organic emitter. In addition to a fluorescent emission, additional contributions can also be obtained in this case by phosphorescent radiation. This can contribute to a significant increase of the internal quantum yield of the layer. The differentiation as to whether a radiation component is of fluorescent or phosphorescent origin can be determined in this case on the basis of time-correlated single photon counting (TCSPC) measurements. By means of TCSPC, the runtime of each individual photon is measured and the distribution of the runtimes is accumulated. Components on a microsecond timescale can be associated in this case with phosphorescent transitions and more rapid transitions can be associated with fluorescent transitions. In each case the mathematic adaptation to the measured intensity curve is observed in this case. This method is known to a person skilled in the art.

The metal atoms $M_1$ and $M_2$ are chosen from the group comprising In, Tl, Sn, Pb, Sb, and Bi. These metals can preferably be used because of their availability, their purchase price, and their capability of implementing a pronounced spin-orbit coupling. Two different metals from the above-mentioned group can also be contained in the bi-nuclear metal complex according to the invention. This group is particularly suitable since the elements listed therein have a particularly high orbital angular momentum, which enables effective phosphorescence transitions in the organic emitters. In addition, these metals are available in high purity at relatively low prices.

In one embodiment, the group can advantageously only comprise Sn, Pb, and Bi. These metals additionally have the advantage that they may also be processed very well out of solutions.

The fluorescent emitter ligands $L_F$, $L_F'$ are organic molecules which can either partially or entirely have aromatic character having delocalized n-electrons. Furthermore, these molecules can have heteroatoms such as N, N—Z, O, S, Se, Si or metals such as Li or Al, Ga or Zn. Z stands in this case for an alkyl or aromatic residue. These molecules display fluorescence as a solid or in solution after electronic excitation, i.e., electronic (S1-S0) singlet-singlet transitions. Phosphorescent transitions (T-S) are not observable at room temperature in these fluorescent emitter ligands because of the quantum mechanics exclusion rules (spin reversal). The lifetime of the fluorescent transitions in the organic fluorescent emitters usable according to the invention can be in a range below 100 ns without approaching the heavy metal atom.

The organic fluorescent emitters $L_F$, $L_F'$ can preferably be C6-C70 heteroaromatics or heteroaromatics; furthermore, they can preferably be C10-O50 aromatics or heteroaromatics. In special applications, the heteroaromatics containing oxygen and nitrogen have proven to be particularly favorable. Furthermore, organic fluorescent emitters can preferably be used within the disclosed method, the triplet state of which is at a distance of greater than or equal to −5 eV and less than or equal to 5 eV from the S0 state. Using these electronic boundary conditions, these fluorescent emitters can result in particularly high quantum yields in the scope of the emitter complex according to the invention. Without being bound by the theory, this is probably because of the steric properties of the selected group, which enables effective coordination/approach to the heavy main group metals.

The terminal ligands $L_T$, $L_T'$ are capable due to their electronic structure of influencing the chromatic properties, in particular here the emission/absorption wavelength of the complex. These ligands differ from the bridging ligands in that the terminal ligands are only each coordinated on one metal atom. The coordination of the terminal ligands on one of the metal atoms can occur in this case via one point of the ligand (mono-dentate), via two points of the ligand (bi-dentate), or via three points of the ligand (tri-dentate). The points of the coordination are preferably in this case heteroatoms or unsaturated bonds in the ligand. Also possible are n-bonded systems.

The bridging ligands $L_V$, $L_V'$ are distinguished in that in each case one ligand interacts with both cores of the bi-nuclear complex. I.e., between a bridging ligand, in each case a σ-bond, n-bond or in general a Coulomb interaction with both metal atoms exists.

Embodiments of the present invention will be described in greater detail hereafter in conjunction with further aspects and embodiments. These can be combined as desired with one another, if the contrary does not result unambiguously from the context.

In one embodiment of the emitter, $M_1$ and $M_2$ can be chosen independently of one another from the group comprising Sb, As, and Bi and n, m=2. A bi-nuclear structure which has as the cores antimony, arsenic, or bismuth atoms has proven to be particularly suitable in combination with a fourfold bridge of both cores via ligands. In this geometry, each core of the complex is coordinated six times (four bridging ligands, one terminal ligand, and one fluorescent emitter per core). This geometry appears to be particularly stable and enables a particularly effective interaction of the fluorescent emitter with the above-mentioned main group metals. In addition, by way of this coordination number, manifold possibilities result for controlling the chromatic properties of the entire emitter complex by way of the selection of the ligands. This is very probably because the bridging ligands, like the terminal ligands, are also capable of providing a contribution to the phosphorescence by interactions with the emitter ligands. The bi-nuclear complex can have in this case two identical, and also two different metal atoms from this group as cores. This constellation appears in this case to enable particularly effective spin-orbit coupling of the metal atom with the fluorescent emitter. Without being bound by the theory, this very probably results due to the similar orbital angular momenta of the above-mentioned metal atoms. Furthermore, this group is particularly preferred, since because of its physical properties, for example, the vaporization temperature or the solubility, it may be processed very well by means of gas phase deposition processes or also wet processes. In a further preferred embodiment, the bi-nuclear complex can also only comprise metal atoms selected from the group Bi and Sb. These two metals are particularly preferred because of their processing capability and because of their toxicological profile. In a further preferred embodiment, the cores of the complex can comprise metal atoms selected from the group Bi and Sb and n, m can be selected from the group comprising 1 or 2.

In a further embodiment of the emitter, $M_1$ and $M_2$ can be chosen independently of one another from the group comprising Pb and Sn and n, m=1 or 2. It has been shown that in particular a bi-nuclear complex which comprises lead and tin is capable of opening an effective phosphorescence channel for the fluorescent emitters. This effective opening of the phosphorescence channel results in this case both due to bridging of the two metal centers via alternately 2, 3, or 4 bridging ligands. This geometric flexibility in the embodiment of the emitter complex results in wide-ranging chromatic tunability of the complex. This is very probably because the bridging ligands can also participate with the now phosphorescent emission, due to wide-ranging interactions with the fluorescent emitters or also due to the control of the electron density of the metal centers, which can have effects on the Lewis acidity. The bi-nuclear metal complex can be constructed as either homonuclear or heteronuclear in this case.

Furthermore, in one embodiment, the emitter can be a homonuclear emitter with $M_1=M_2=Bi$. Bismuth has proven to be particularly suitable because of its economic and processing properties. A variety of complex compounds exist, which may be processed particularly efficiently with organic fluorescent emitters in the scope of wet processes or gas phase processes. Although bismuth directly follows lead in the periodic system, it has very different physiological properties. Because it can only be absorbed with difficulty via the gastrointestinal tract, poisoning with bismuth is rather rare. In contrast, salts of bismuth are used in medicine to treat stomach complaints or syphilis. It was also used as a contrast agent for x-ray examinations. Only the isotope of bismuth having the mass 209 occurs naturally. It is a radioactive α-emitter with a half-life time of $1.9 \times 10^{19}$ years. From the long half-life time, an activity of 0.0033 Bq results for 1 kg. This is approximately 10,000,000 times less than that of potassium, which occurs in organisms. A kilogram of potassium naturally contains 0.012%, i.e., 0.12 g of the radioactive isotope 40K with a half-life time $t_{1/2}$ of $1.248 \times 10^9$ years seconds and has an atomic mass of 39.96. A radioactivity of 31825 Bq results therefrom. Therefore, the radioactivity of bismuth is negligible for practical applications and would not even be detectable by a human holding a Geiger counter. Bismuth has, in contrast to iridium (3/2) and europium (5/2), a nuclear spin of (9/2). This is capable of coupling with unpaired electrons, which are located on ligands. These properties and the fact that bismuth deposits are subject to practically no restriction in comparison to the iridium deposits can result in a dramatically better educt cost situation.

In one embodiment, the distances between at least one metal atom and the ligands $L_V$, $L_{V'}$, $L_T$, $L_{T'}$ coordinated thereon can be greater than or equal to 2.2 Å and less than or equal to 3.0 Å. These distances between a metal atom and the ligands coordinated thereon have proven to be effective for opening an effective phosphorescence channel of the fluorescent emitter. In addition, these distances similarly allow effective influencing of the phosphorescence emission by the terminal and bridging ligands, which are not directly capable of phosphorescence. Without being bound by the theory, this can occur in the scope of these distances due to effective spin coupling of the heavy metal atom. In addition, a further modification of the emission/absorption wavelength can be performed by the distances of the terminal and bridging ligands. This is very probably due to a further electronic interaction of the terminal and bridging ligands, which are not capable of fluorescence, with the fluorescent ligand. This further electronic interaction is influenced in this case essentially by the distance of the individual interaction partners. The distances in this case between at least one metal atom and the ligands $L_V$, $L_{V'}$, $L_T$, $L_{T'}$ coordinated thereon can preferably be greater than or equal to 2.25 Å and less than or equal to 2.95 Å, and furthermore preferably greater than or equal to 2.3 Å and less than or equal to 2.9 Å. The distance is defined in this case as the smallest route between one of the two metal atoms and the relevant ligand. This distance may be obtained, for example, via an x-ray analysis on single crystals of the observed complex.

According to a further embodiment of the emitter, at least one of $L_F$, $L_{F'}$ can be chosen from the group comprising substituted or non-substituted mono-, di-, or tri-dentate C6-C70 N-heteroaromatics. This group of organic fluorescent emitters results in interaction with the bi-nuclear complexes according to the invention in a particularly high phosphorescence contribution of the emitters, which are otherwise solely fluorescent at room temperature. Without being bound by the theory, in particular the above-selected size of the fluorescent ligands can allow particularly good approach and coordination to the bi-nuclear complex. In particular, it has also been shown that a mono-dentate or multi-dentate coordination on one of the heavy main group metals via a nitrogen results in particularly efficient interaction. This results in a high phosphorescence contribution of the fluorescent emitters and a very chemically stable overall complex. The fluorescent emitters can be embodied in this case as both fully aromatic and also only partially aromatic. In addition, the N-heteroaromatics can also have still further heteroatoms, for example, O or S, in addition to the at least one nitrogen.

In one embodiment of the emitter, at least one of $L_F$, $L_{F'}$ can be chosen from the group comprising substituted or non-substituted C6-C70 2,2'-bipyridines. In particular the group of 2,2'-bipyridines appears to be suitable for particularly efficient interaction with a heavy main group metal due to their geometric and electrical structure. Without being bound by the theory, this very probably results due to the bi-dentate coordination of the fluorescent emitter on the main group metal. In this case, both the distance of the two nitrogens, and also the incorporation thereof in an aromatic system, appear to enable the opening of the phosphorescence channel by the orbital angular momentum of the heavy metal atom particularly well. The usable 2,2'-bipyridines can be substituted in this case at any bond-capable point of their basic framework. Possible substituents can be selected from the group comprising substituted and unsubstituted heterocycles, for example, furan, thiophene, pyrrole, oxazole, thiazole, imidazole, isoxazole, isothiazole, pyrazole, pyridine, pyrazine, pyrimidine, 1,3,6-triazine, pyrylium, alpha-pyrone, gamma-pyrone, benzofuran, benzothiophene, indole, 2H-isoindole, benzothiazole, 2-benzothiophene, 1H-benzimidazole, 1H-benzotriazole, 1,3-benzoxazole, 2-benzofuran, 7H-purine, quinoline, isoquinoline, quinazoline, quinoxaline, phthalazine, 1,2,4-benzotriazine, pyrido[2,3-d]pyrimidine, pyrido[3,2-d]pyrimidine, pteridine, acridine, phenazine, benzo[g]pteridine, 9H-carbazole, and bipyridine, and the derivatives thereof. The two fluorescent emitters can both be selected in this case independently from one another from the above-mentioned group and/or can consist in special individual cases of the same chemical compound. In this case, $L_F = L_F'$. The fluorescent emitters can preferably also be chosen from the group of C10-C60 and furthermore preferably from the group of C15-055 2,2'-bipyridines.

In one embodiment, at least one of $L_F$, $L_F'$ can be chosen from the group comprising substituted or non-substituted mono-, di-, or tri-dentate C6-C70 N-heteroaromatics comprising at least one carbazole unit. It has been shown that particularly effective coupling to the heavy metal atoms can be achieved by fluorescent emitters which have nitrogens as heteroatoms and additionally have a carbazole unit. These fluorescent emitters can have a suitable tunable wavelength spectrum as a function of the heavy metal atom, the selected basic framework of the fluorescent emitter, and the remaining, non-fluorescent emitter. The carbazole unit appears to have a particularly suitable electronic structure for this purpose. In a special embodiment, this can relate, for example, to bi-dentate 2,2'-bipyridines, which bear at least one carbazole unit. This can result in particularly effective and long-lived emitters.

In a further embodiment, at least one of $L_F$, $L_F'$ can be chosen from the group comprising 4,7-di(9H-carbazol-9-yl)-1,10-phenanthroline, 2,6-bis(3-(9H-carbazol-9-yl)phenyl)pyridine, and 3,5-bis(3-(9H-carbazol-9-yl)phenyl)pyridine. This group of emitters has proven to be particularly suitable in the scope of production by vacuum processes or wet processes. The bi-nuclear complexes which have fluorescent emitters from the above-mentioned group may be processed by standard methods and result in particular in stable, long-lived layers. Very probably due to the electronic structure of these fluorescent emitters, particularly good interaction results with the heavy metal atoms and the remaining ligands, which results in particularly high quantum yield. Without being bound by the theory, this is very probably based on the suitable molecular size and the carbazole units within these structures. These fluorescent emitters can additionally be substituted at any bonding-capable point of their basic framework by the above-mentioned substituent group.

In one embodiment, at least one of $L_V$, $L_V'$ can be chosen from the group comprising fluorinated or non-fluorinated C2-C30 O—, S—, N—, heteroalkyl, heterocycloalkyl, or heteroaromatics. This size of bridging ligands can contribute both to effective bridging of the two metal centers and also to effective interaction of the ligands themselves with the fluorescent emitters. In this manner, stable bi-nuclear complexes are obtained which are stable enough to be able to be processed using the greatly varying standard methods of organic electronics. Without being bound by the theory, these advantageous effects result due to the steric properties of the above-mentioned bridging ligands. Larger ligands, i.e., ligands having a higher number of carbon atoms, can be disadvantageous, since effective bridging of the metal centers is no longer possible here. In a special embodiment of the invention, all bridging ligands can be chosen from the above-mentioned group. In a further embodiment according to the invention, all bridging ligands can additionally consist of only one compound from the above-mentioned group. In this way, in particular symmetric bridging can result, which can result in a symmetrical electronic environment as a function of the selection of the terminal ligands and the fluorescent emitters. In particular, the bridging ligands can also be fluorinated or non-fluorinated C2-C25, furthermore preferably O—, S—, N—, heteroalkyl, heterocycloalkyl, or heteroaromatics C2-C20.

In a further embodiment, the emitter can correspond to following formula II,

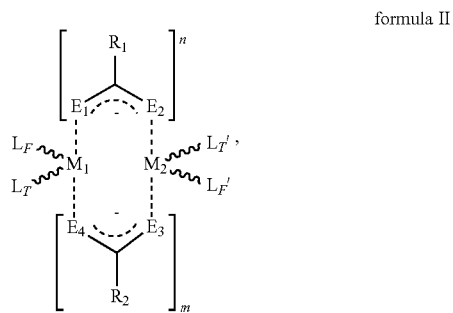

formula II wherein
$R_1$, $R_2$ are chosen independently of one another from the group comprising fluorinated or non-fluorinated C1-C30 alkyl, cycloalkyl, aryl, heteroalkyl, heterocycloalkyl, heteroaryl; $E_1$, $E_2$, $E_3$, $E_4$ are chosen independently of one another from the group comprising O, S, NR, wherein R=H, D. The bridging of the two metal cores of the complex via above-specified bridging ligands advantageously occurs in this embodiment via 0, S, NR heteroatoms or heterocompounds, wherein the ligands are at least formally provided with a single negative charge. Due to this type of bridging ligands, very stable bi-nuclear complexes may be obtained, which enable effective coupling of the orbital angular momentum of both metal atoms to the fluorescent emitters. Without being bound by the theory, in particular the bi-dentate hetero-bridging ligands can contribute to a particular electronic structure of the overall complex, which results in particularly effective opening of the phosphorescence channel in the fluorescent emitters. In this manner, particularly high quantum yields of the complex may be achieved. As a function of the observed heavy main group metals, in above-specified formula II, for the elements Pb and Sn, n, m=1 or 2 results and for the elements Sb, As, and Bi, n, m=2 results. The complexes according to above-specified formula II can result in particularly stable and efficient phosphorescent emitters.

According to a further embodiment, at least one of the ligands $L_V$, $L_V'$ can be chosen from the group comprising fluorinated or non-fluorinated aliphatic or aromatic C2-C30 carboxylates. The bridging of the two metal centers of the bi-nuclear complex via relatively short-chain carboxylates is very probably capable of ensuring a suitable distance between the two metal centers. Furthermore, the bridging via oxygens appears to provide a suitable contribution by the bridging ligands, which results in particularly favorable interactions between the metal centers and the fluorescent emitters and between the fluorescent emitters and the bridging ligands. Thus, the emission and absorption behavior of the overall complex can also be influenced by means of the bridging ligands. In a further preferred embodiment, all bridging ligands can be chosen from the above-mentioned group. Furthermore, it can be favorable if all bridging ligands correspond to a compound from the above-specified group. This can result in particularly favorable, symmetrical complexes, which enable a high quantum yield.

In one embodiment, at least one of the ligands $L_V$, $L_V'$ is chosen from the group comprising C2-C30 acetate, fluoroacetate, fluorobenzoate, fluoromethylbenzoate, fluoromethylfluorobenzoate, di-fluoromethyl-benzoate, di-fluoromethyl-fluorobenzoate. This special group of fluorinated or non-fluorinated oxygen-containing, bridging ligands can contribute to particularly effective bridging of the two metal centers. This is very probably because of the special electronic structure of the carboxylate groups and the steric embodiment of the ligands. These ligands can also interact in particular via the metal atoms with the fluorescent emitters and thus also determine the phosphorescence properties of the overall complex. In addition, the electronic structure of the overall complex may be influenced by the degree of fluorination of the individual ligand basic frameworks. The prefix "fluoro" includes in this case both a single fluorination and also perfluorination of the compounds. In a further embodiment, all bridging ligands can also be chosen from the above-mentioned group. In addition, it can also be advantageous if all bridging ligands correspond to the same compound from the above-mentioned group, i.e., all bridging ligands are chemically identical.

Furthermore, the following are listed as examples of preferred bridging ligands $L_V$, $L_V'$:

fluorinated benzoates, e.g., 2-(trifluoromethyl)benzoate; 3,5-difluorobenzoate; 3-hydroxy-2,4,6-triiodobenzoate; 3-fluoro-4-methylbenzoate; 3-(trifluoromethoxy) benzoate; 4-(trifluoromethoxy)benzoate; 4-chloro-2,5-difluorobenzoate; 2-chloro-4,5-difluorobenzoate; 2,4,5-trifluorobenzoate; 2-fluorobenzoate; 4-fluorobenzoate; 2,3,4-trifluorobenzoate; 2,3,5-trifluorobenzoate; 2,3-difluorobenzoate; 2,4-bis(trifluoromethyl)benzoate; 2,4-difluorobenzoate; 2,5-difluorobenzoate; 2,6-bis(trifluoromethyl)benzoate; 2,6-difluorobenzoate; 2-chloro-6-fluorobenzoate; 2-fluoro-4-(trifluoromethyl)benzoate; 2-fluoro-5-(trifluoromethyl)benzoate; 2-fluoro-6-(trifluoromethyl)benzoate; 3,4,5-trifluorobenzoate; 3,4-difluorobenzoate; 3,5-bis(trifluoromethyl)benzoate; 3-(trifluoromethyl)benzoate; 3-chloro-4-fluorobenzoate; 3-fluoro-5-(trifluoromethyl)benzoate; 3-fluorobenzoate; 4-fluoro-2-(trifluoromethyl)benzoate; 4-fluoro-3-(trifluoromethyl)benzoate; 5-fluoro-2-methylbenzoate; 2-(trifluoromethoxy)benzoate; 2,3,5-trichlorobenzoate; 4-(trifluoromethyl)benzoate; pentafluorobenzoate; 2,3,4,5-tetrafluorobenzoate; 2,3,5,6-tetrafluoro-4-(trifluoromethyl)benzoate;

fluorinated or non-fluorinated phenyl acetates, e.g., 2-fluoro-phenyl acetate; 3-fluoro-phenyl acetate; 4-fluoro-phenyl acetate; 2,3-difluoro-phenyl acetate; 2,4-difluoro-phenyl acetate; 2,6-difluoro-phenyl acetate; 3,4-difluoro-phenyl acetate; 3,5-difluoro-phenyl acetate; pentafluoro-phenyl acetate; 2-chloro-6-fluoro-phenyl acetate; 2-chloro-3,6-difluoro-phenyl acetate; 3-chloro-2,6-difluoro-phenyl acetate; 3-chloro-4-fluoro-phenyl acetate; 5-chloro-2-fluoro-phenyl acetate; 2,3,4-trifluoro-phenyl acetate; 2,3,5-trifluoro-phenyl acetate; 2,3,6-trifluoro-phenyl acetate; 2,4,5-trifluoro-phenyl acetate; 2,4,6-trifluoro-phenyl acetate; 3,4,5-trifluoro-phenyl acetate; 3-chloro-2-fluoro-phenyl acetate; α-fluoro-phenyl acetate; 4-chloro-2-fluoro-phenyl acetate; 2-chloro-4-fluoro-phenyl acetate; α,α-difluoro-phenyl acetate; ethyl 2,2-difluoro-2-phenyl acetate; and fluorinated or non-fluorinated acetates, e.g., methyl-trifluoroacetate; allyl-trifluoroacetate; ethyl-trifluoroacetate; isopropyl-trifluoroacetate; 2,2,2-trifluoroethyl-trifluoroacetate; difluoroacetate; trifluoroacetate; methyl-chlorodifluoroacetate; ethyl-bromodifluoroacetate; chlorodifluoroacetate; ethyl-chlorofluoroacetate; ethyl-difluoroacetate; (3-chlorophenyl)-difluoracetate; (3,5-difluorophenyl)-difluoroacetate; (4-butylphenyl)difluoroacetate; (4-tert-butylphenyl)difluoroacetate; (3,4-dimethylphenyl)-difluoroacetate; (3-chloro-4-fluorophenyl)-difluoroacetate; (4-chlorophenyl)-difluoroacetate; 2-biphenyl-3',5'-difluoroacetate; 3-biphenyl-3',5'-difluoroacetate; 4-biphenyl-3',5'-difluoroacetate; 2-biphenyl-3',4'-difluoroacetate; 3-biphenyl-3',4'-difluoroacetate; 4-biphenyl-3',4'-difluoroacetate, and 2,2-difluoro-propionate or the higher homologs thereof, respectively.

In one embodiment, at least one of the ligands $L_T$, $L_T'$ can be chosen from the group comprising fluorinated or non-fluorinated aliphatic or aromatic C2-C30 alcoholates, carboxylates, benzoates, or acetylacetonates. These particularly preferred terminal ligands are each only coordinated on one of the metal atoms of the bi-nuclear complex. Very probably because of the steric requirements of these terminal ligands and the coordination on the metal center via an oxygen, particularly advantageous interactions also result with the fluorescent emitters, so that the emissive and also absorbent properties of the complex can be influenced via the terminal ligands. In particular the oxygen or oxygens also appear to be suitable as coordination points to the metal atom. Stable bi-nuclear complexes result, which achieve a high quantum yield and can result in stable layers and long-lived organic components. In a special embodiment, all terminal ligands can also be chosen from the above-mentioned group. Furthermore, it can be advantageous if the two terminal ligands correspond to only one compound from the above-mentioned group. This can result in particularly symmetrical bi-nuclear metal complexes.

In one embodiment, at least one of the ligands $L_T$, $L_T'$ can be chosen from the group comprising C2-C30 acetate, fluoroacetate, fluorobenzoate, fluoromethylbenzoate, fluoromethyl fluorobenzoate, di-fluoromethyl-benzoate, di-fluoromethyl-fluorobenzoate. The bi-dentate terminal ligands can result in particularly efficient phosphorescent emitters. This can be because the coordination of a terminal ligand via two oxygen atoms on a metal center results in an electronically favorable situation, in which the terminal ligand is capable of also influencing the phosphorescence properties of the fluorescent emitter. In a further embodiment, both terminal ligands can be chosen from the above-mentioned group. In addition, in a special embodiment, both terminal ligands can correspond to the same compound from the above-mentioned group. This can result in advantageous electrical properties of the overall complex.

Furthermore, the following are listed as examples of preferred terminal ligands $L_T$, $L_T'$:

fluorinated benzoates, e.g., 2-(trifluoromethyl)benzoate; 3,5-difluorobenzoate; 3-hydroxy-2,4,6-triiodobenzoate; 3-fluoro-4-methylbenzoate; 3-(trifluoromethoxy)benzoate; 4-(trifluoromethoxy)benzoate; 4-chloro-2,5-difluorobenzoate; 2-chloro-4,5-difluorobenzoate; 2,4,5-trifluorobenzoate; 2-fluorobenzoate; 4-fluorobenzoate; 2,3,4-trifluorobenzoate; 2,3,5-trifluorobenzoate; 2,3-difluorobenzoate; 2,4-bis(trifluoromethyl)benzoate; 2,4-difluorobenzoate; 2,5-difluorobenzoate; 2,6-bis(trifluoromethyl)benzoate; 2,6-difluorobenzoate; 2-chloro-6-fluorobenzoate; 2-fluoro-4-(trifluoromethyl)benzoate; 2-fluoro-5-(trifluoromethyl)benzoate; 2-fluoro-6-(trifluoromethyl)benzoate; 3,4,5-trifluorobenzoate; 3,4-difluorobenzoate; 3,5-bis(trifluoromethyl)benzoate; 3-(trifluoromethyl)benzoate; 3-chloro-4-fluorobenzoate; 3-fluoro-5-(trifluoromethyl)benzoate; 3-fluorobenzoate; 4-fluoro-2-(trifluoromethyl)benzoate; 4-fluoro-3-(trifluoromethyl)benzoate; 5-fluoro-2-methylbenzoate; 2-(trifluoromethoxy)benzoate; 2,3,5-trichlorobenzoate; 4-(trifluoromethyl)benzoate; pentafluorobenzoate; 2,3,4,5-tetrafluorobenzoate; 2,3,5,6-tetrafluoro-4-(trifluoromethyl)benzoate;

fluorinated or non-fluorinated phenyl acetates, e.g., 2-fluoro-phenyl acetate; 3-fluoro-phenyl acetate; 4-fluoro-phenyl acetate; 2,3-difluoro-phenyl acetate; 2,4-difluoro-phenyl acetate; 2,6-difluoro-phenyl acetate; 3,4-difluoro-phenyl acetate; 3,5-difluoro-phenyl acetate; pentafluoro-phenyl acetate; 2-chloro-6-fluoro-phenyl acetate; 2-chloro-3,6-difluoro-phenyl acetate; 3-chloro-2,6-difluoro-phenyl acetate; 3-chloro-4-fluoro-phenyl acetate; 5-chloro-2-fluoro-phenyl acetate; 2,3,4-trifluoro-phenyl acetate; 2,3,5-trifluoro-phenyl acetate; 2,3,6-trifluoro-phenyl acetate; 2,4,5-trifluoro-phenyl acetate; 2,4,6-trifluoro-phenyl acetate; 3,4,5-trifluoro-phenyl acetate; 3-chloro-2-fluoro-phenyl acetate; α-fluoro-phenyl acetate; 4-chloro-2-fluoro-phenyl acetate; 2-chloro-4-fluoro-phenyl acetate; α,α-difluoro-phenyl acetate; ethyl 2,2-difluoro-2-phenyl acetate; and fluorinated or non-fluorinated acetates, e.g., methyl-trifluoroacetate; allyl-trifluoroacetate; ethyl-trifluoroacetate; isopropyl-trifluoroacetate; 2,2,2-trifluoroethyl-trifluoroacetate; difluoroacetate;

trifluoroacetate; methyl-chlorodifluoroacetate; ethyl-bromodifluoroacetate; chlorodifluoroacetate; ethyl-chlorofluoroacetate; ethyl-difluoroacetate; (3-chlorophenyl)-difluoroacetate; (3,5-difluorophenyl)-difluoroacetate; (4-butylphenyl)difluoroacetate; (4-tert-butylphenyl)difluoroacetate; (3,4-dimethylphenyl)-difluoroacetate; (3-chloro-4-fluorophenyl)-difluoroacetate; (4-chlorophenyl)-difluoroacetate; 2-biphenyl-3',5'-difluoroacetate; 3-biphenyl-3',5'-difluoroacetate; 4-biphenyl-3',5'-difluoroacetate; 2-biphenyl-3',4'-difluoroacetate; 3-biphenyl-3',4'-difluoroacetate; 4-biphenyl-3',4'-difluoroacetate, and 2,2-difluoropropionate or the higher homologs thereof, respectively.

Other embodiments provide an emitter, wherein each of the ligands $L_V$, $L_V'$, $L_T$, $L_T'$ is chosen from the group comprising C2-C30 acetate, fluoroacetate, fluorobenzoate, fluoromethylbenzoate, fluoromethyl fluorobenzoate, di-fluoromethyl-benzoate, di-fluoromethyl-fluorobenzoate. Particularly efficient metal complexes can result in that the bridging ligands and the terminal ligands are chosen from the above-mentioned group, which is composed of bidentate oxygen compounds. These compounds can be both aliphatic and also partially aromatic in this case. It appears in this case that the attachment of the ligands via the oxygens to the metal atoms is capable of providing a stable complex to a high degree. Furthermore, it appears that a special interaction with the fluorescent emitters can be obtained via the oxygens, which has the result that the emissive and absorbent properties of the fluorescent emitters are also influenced by the ligands. In this manner, the chromatic properties of the overall complex may be adapted. In a special embodiment of the invention, both the bridging ligands and also the terminal ligands can correspond to a compound from the above-mentioned group. Highly symmetric coordinated metal complexes may thus be obtained, which are capable of providing particularly high quantum yields.

Other embodiments provide a method for producing organic electric layers having organic emitters which are phosphorescent at room temperature is wherein the organic phosphorescent emitters according to the invention are provided within a layer on a substrate. The bi-nuclear emitters according to the invention can be suitable in particular for the purpose of being provided in the scope of layers. For this purpose, either the bi-nuclear emitters can be deposited in their structure according to the invention as layers or the structure according to the invention can be formed in situ on the surface of a substrate. For this purpose, it is possible, on the one hand, that the complete complex comprising the two metal atoms, the terminal and bridging ligands, and the fluorescent emitters is deposited on a surface as a layer. Furthermore, it can also be according to the invention that only a bimetallic metal complex having terminal and bridging ligands is deposited and subsequently the fluorescent emitters are coordinated on the two-core complex in a downstream reaction step on the surface of the substrate. Without being bound by the theory, in the method according to the invention, the organic emitter is brought into the vicinity of the main group metal in this case. The arrangement of the ligands of the metal complex subsequently changes. This is caused by van-der-Waals, Coulomb, Π-π, or σ interactions of the organic emitter with the metal. A σ interaction is not necessary to implement the phosphorescence, but can also be implemented. The coordination sphere of the metal can be expanded by the vicinity of the organic emitter. One single ligand or multiple ligands can also be substituted for the organic emitter. Furthermore, it is also possible that the number of the ligands is reduced by the change of the coordination sphere. For example, this is due to the displacement of one or more ligands by the accommodation of the fluorescent organic emitter. As a result, a phosphorescent organic emitter having the structure according to the invention is obtained. Moreover, it is additionally possible to select a production variant in which the complex according to the invention is first formed by reaction on the substrate surface. In this case, for example, mono-nuclear metal complexes can be caused to react with the terminal and bridging ligands according to the invention and the fluorescent emitters on a substrate, wherein a bi-nuclear complex having the structure according to the invention first arises. It is important that without damaging the compounds/complexes used, after the reaction a bi-nuclear complex having the structure set forth according to the invention results.

The metal complex and the organic fluorescent emitter can preferably be deposited on a carrier substrate as an amorphous layer by means of co-evaporation, rotation coating, curtain coating, a doctor blade, or printing. Particularly preferably, the amorphous layer can be produced by means of gas phase deposition or wet processes. By means of these methods, the metal complex and the organic fluorescent emitter can be deposited together and thus form the amorphous layer. Both substances can be sublimated in the scope of a co-evaporation method in this case from different sources while using thermal energy. By means of these methods, particularly homogeneous and uniform layers are obtained. Solvent processes can preferably be carried out so that the components are deposited from a solvent on a substrate. This can simplify the process control and enable more cost-effective production. In addition, still further materials, for example, matrix materials, which are not coordinated on the metal atom, can be dissolved in the solvent and/or can also be deposited within the layer. These matrix materials can additionally also be vapor deposited from further sources.

In addition to the bi-nuclear metal complex, in the scope of the disclosed method, still further, non-coordinating matrix materials can be deposited within the layer. This matrix material or these matrix materials can influence the electronic conductivity of the layer or can have influence in general on the mobility of the organic emitter or the metal complex, for example. Suitable matrix materials can be selected from the group 2,2',7,7'-tetrakis(carbazol-9-yl)-9,9-spirobifluorene; 2,7-bis(carbazol-9-yl)-9,9-ditolylfluorene; 9,9-bis[4-(carbazol-9-yl)-phenyl]fluorene; 2,7-bis(carbazol-9-yl)-9,9-spirobifluorene; 1,4-bis(triphenylsilyl)benzene; 1,3-bis(triphenylsilyl)benzene; bis(4-N,N-diethylamino-2-methylphenyl)-4-methylphenylmethane; 2,7-bis(carbazol-9-yl)-9,9-dioctylfluorene; 4,4"-di(triphenylsilyl)-p-terphenyl; 4,4'-di(triphenylsilyl)-biphenyl; 9-(4-tert-butylphenyl)-3,6-bis(triphenylsilyl)-9H-carbazole; 9-(4-tert-butylphenyl)-3,6-ditrityl-9H-carbazole; 9-(4-tert-butylphenyl)-3,6-bis(9-(4-methoxyphenyl)-9H-fluoren-9-yl)-9H-carbazole; 2,6-bis(3-(9H-carbazol-9-yl)phenyl)pyridine; 3,5-bis(3-(9H-carbazol-9-yl)phenyl)pyridine, triphenyl(4-(9-phenyl-9H-fluoren-9-yl)phenyl)silane; 9,9-dimethyl-N,N-diphenyl-7-(4-(1-phenyl-1H-benzo[d]imidazol-2-yl)phenyl)-9H-fluorene-2-amine; 3,5-bis(3-(9H-carbazol-9-yl)phenyl)pyridine; 9,9-spirobifluoren-2-yl-diphenyl-phosphine oxide; 9,9'-(5-(triphenylsilyl)-1,3-phenylene)bis(9H-carbazole); 4,4,8,8,12,12-hexa-p-tolyl-4H-8H-12H-12C-azadibenzo[cd,mn]pyrene; 2,2'-bis(4-(carbazol-9-yl)phenyl)-biphenyl; 2,8-bis(diphenylphosphoryl)dibenzo[b,d]thiophene; bis(2-methylphenyl)diphenylsilane; bis[3,5-di(9H-carbazol-9-yl)phenyl]diphenylsilane; 3,6-bis(carbazol-9-yl)-9-(2-ethylhexyl)-9H-carbazole; 3-(diphenylphosphoryl)-9-(4-(diphenylphosphoryl)phenyl)-9H-carbazole; 3,6-bis[(3,5-diphenyl)phenyl]-9-phenyl-carbazole; 2,8-di(9H-carbazol-9-yl)dibenzo[b,d]thiophene; 10-(4'-(diphenylamino)biphenyl-4-yl)acridin-9(10H)-one; 2,7-bis(diphenylphosphoryl)-9,9'-spirobi[fluorene]; 1,4-bis((9H-carbazol-9-yl)methyl)benzene; bis-4-(N-carbazolyl)phenyl)phenylphosphine oxide; 2,7-bis(diphenylphosphoryl)-9-(4-diphenylamino)phenyl-9'-phenyl-fluorene; di(4-(6H-indolo[3,2-b]quinoxalin-6-yl)phenyl)diphenylsilane; di(4-(6H-indolo[3,2-b]quinoxalin-6-yl)phenyl)diphenylmethane; bis[3,5-di(9H-carbazol-9-yl)phenyl]diphenylsilane; 2,6,14-tris(carbazol-9-yl)triptycene; 2,6,14-tris(diphenylphosphine-oxide)triptycene; 2,6,14-tris(diphenyl-amino)triptycene; 2,7-bis(diphenylphosphoryl)-9-phenyl-9H-carbazole; tris[4-(9-phenylfluoren-9-yl)phenyl]aminebiphenyl-3-amine); 2,7-bis(diphenylphosphoryl)spiro[fluorene-7,11'-benzofluorene].

In addition, in the disclosed method, the deposition of the metal complex and the organic fluorescent emitter can be performed separately and by means of a co-evaporation method, wherein the deposition rate of the organic electric layer can be greater than or equal to 0.1 Å/s and less than or equal to 200 Å/s. The opening of the phosphorescence channel of the organic emitter is coupled in the case of the separate deposition to the coordination change of the heavy main group metal by the accommodation of or the adduct formation with the organic emitter. The spatial proximity of the emitter to the metal enables in this case a spin-orbit coupling, which results in a reduced lifetime of excited triplet states of the organic emitter. Surprisingly, it has been found that these distances between emitter and metal can also be induced by means of co-evaporation. This is surprising because the most defined possible distance, for example, as provided in single crystals or in crystalline structures, would be expected as a requirement for the existence of high quantum yields. However, this may not be expected in the case of a production by means of co-evaporation, since the individual molecules are deposited disordered, amorphously, within a layer. Solvent-free layers having longer service life may be obtained by this method. The preferred deposition rate can contribute in this case to a uniform layer structure. Lower deposition rates are not according to the invention, since these would make the production significantly more costly as a result of the time consumption. Furthermore, higher rates are not according to the invention, since the quantum yield can be reduced as a result of an inadequate distance setting between metal and organic emitters. The deposition rate can preferably furthermore be greater than or equal to 0.1 Å/s and less than or equal to 150 Å/s and furthermore preferably greater than or equal to 1.0 Å/s and less than or equal to 100 Å/s.

Other embodiments provide an organic electric layer which is produced according to the method according to the invention. By means of the method according to the invention, layers may be produced in organic electric components which are capable of emission and conversion of light. The layers can have a layer thickness of greater than or equal to 0.5 nm and less than or equal to 500 μm and can be applied by means of the above-described methods. In the scope of co-evaporation processes, the layer is obtained by the direct application of the substances from the gas phase, while in contrast in wet processes, the layer is obtained after evaporation of the solvent or solvents. The emitter layers obtained according to the invention can be of neutral or ionic nature in this case and therefore can display emission behavior typical for OLED or OLEEC.

Other embodiments provide the use of the layer as an active layer in an organic electric component for converting electric current into light or light into electric current or light into light of another wavelength is according to the invention. The layer according to the invention may accordingly be used for obtaining current by absorption of light waves and also for generating light by means of an electric current. Furthermore, the layer can also be used for converting light waves into light waves of another wavelength. This is performed, for example, by absorbing light quanta and emitting light quanta of another wavelength.

Other embodiments provide an organic semiconductor component selected from the group comprising photodiodes, solar cells, organic light-emitting diodes, light-emitting electrochemical cells containing a phosphorescent emitter according to the invention. The described method and the layers thereby producible can be used accordingly for absorbent components such as photodiodes or solar cells. Furthermore, the layers can also be used for photoconversion layers in photovoltaics or sensors. The method is compatible with the standard production steps of these components and cost-effective, long-lived, and efficient components may be obtained in this manner.

With regard to further advantages and features of the above-described organic semiconductor components, reference is hereby explicitly made to the explanations in conjunction with the emitters according to the invention, the layer according to the invention, and the method according to the invention. Features and advantages according to the invention of the emitters according to the invention are also to be applicable and are considered to be disclosed for the layers according to the invention, the method according to the invention, and the organic semiconductor components according to the invention and vice versa. All combinations of at least two of the features disclosed in the description and/or the claims also fall under the invention.

The above-described properties, features, and advantages of this invention and the manner in which these are achieved will become clearer and more explicitly comprehensible in conjunction with the following description of the exemplary embodiments, which are explained in greater detail below in conjunction with the drawings.

The structure of components which can contain bi-nuclear emitters according to the method according to the invention is shown in the figures, as discussed below in the context of the following example.

EXAMPLES

Example 1: hexakis-(μ-pentafluorobenzoato-k2O:O')bis[(4,7-di(9H-carbazol-9-yl)-1,10-phenanthroline-k2 N:N')bismuth(III)]— complex (1)

Figure 2:
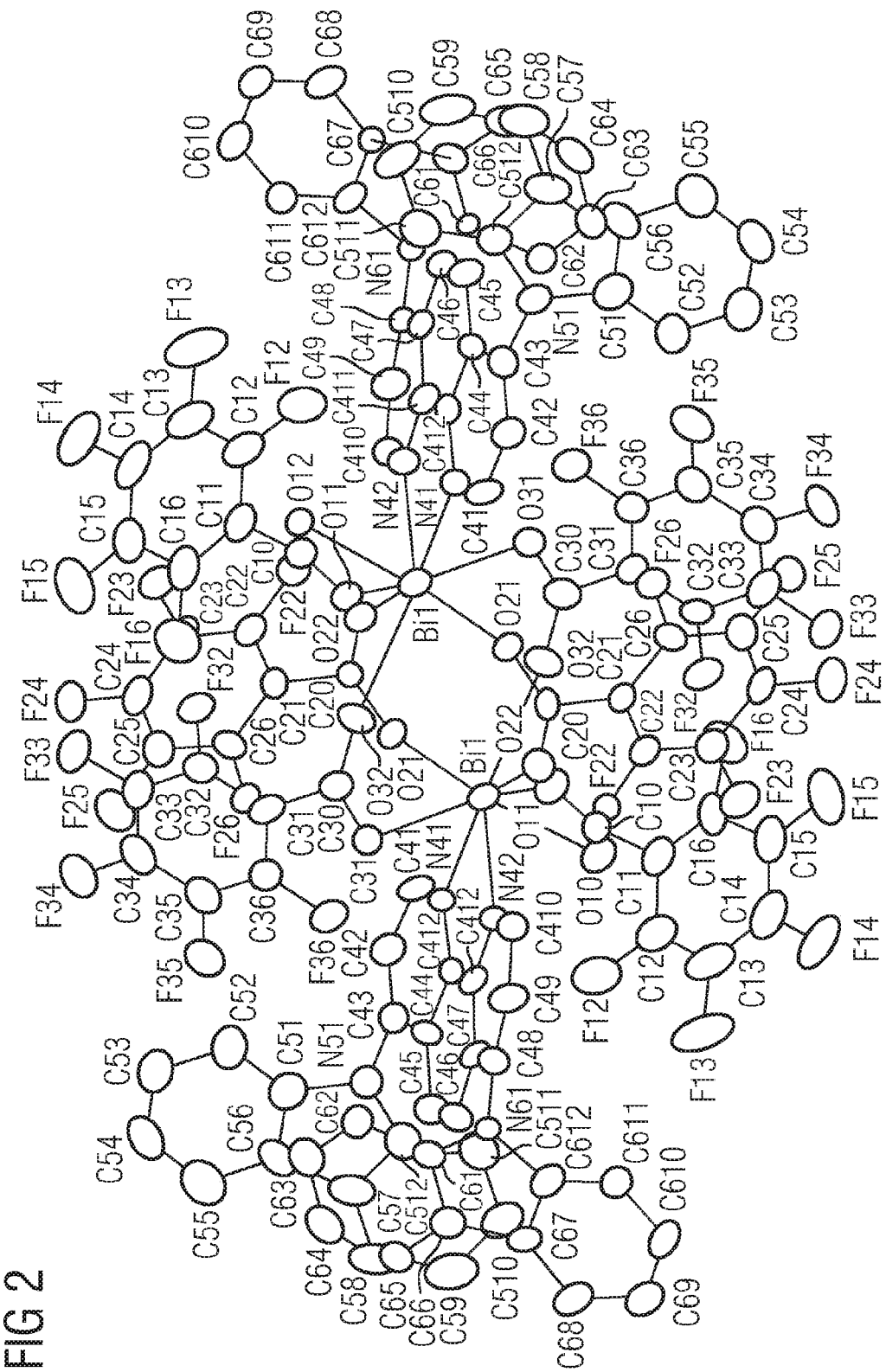
FIG. 2 shows an altered illustration of the structure of the complex 1, now with a view of the coordination of the terminal and bridging ligands on the bismuth atoms.

FIG. 1 and FIG. 2 show an example of a bi-nuclear phosphorescent emitter according to the invention. FIG. 1 shows in this case a bi-nuclear phosphorescent complex according to the invention, here hexakis-(p-penta-fluorobenzoato-k2O:O')bis[(4,7-di(9H-carbazol-9-yl)-1,10-phenanthroline-k2 N:N')bismuth(III)], with terminal and bridging ligands, and also as emitter ligands two BUPH1. FIG. 1 illustrates in this case the view of the BUPH1 ligands coordinated on the bismuth atoms. The crystal structure data for the complex (1) are reproduced in tables 1-3.

A second figure (FIG. 2) allows the view of the coordination of the terminal and bridging ligands on the bismuth atoms.

Production of Complex (1):
Crystallization:

In a Schlenk tube, bismuth(III) pentafluorobenzoate (24.8 mg; 0.0293 mmol) and BUPH1 (15 mg; 0.0293 mmol) are dissolved in 10 ml dichloromethane (molar ratio 1:1). The solution is stirred for approximately 30 minutes at room temperature. Crystals suitable for x-ray structure analysis are obtained from dichloromethane/n-hexane at −18° C. The crystals obtained display, upon irradiation with ultraviolet light, for example, of the wavelength 365 nm, a strong yellow-green phosphorescence, which is not obtainable under the same conditions from pure BUPH1.

Production of the Emission Layers:

The complex 1-emitters according to the invention are deposited as a homogeneous layer having a thickness of 100 nm on a glass substrate by spin coating and then heated for 10 minutes at 100° C.; the concentration of the complex in the toluene solution is approximately 20 mg/mL. The required rotational speed is dependent on the degree of dilution and the specific spin coater (100 nm at 1000 RPM). The layer displays phosphorescence after excitation using ultraviolet light.

Further experiments have shown that high-boiling-point solvents such as anisole and phenetole are also suitable for producing the homogeneous layers.

Example 2: hexakis-(μ-trifluoroacetate-k2O:O')bis[(4,7-di(9H-carbazol-9-yl)-1,10-phenanthroline-k2 N:N')bismuth(III)]-complex (2)

Figure 3:
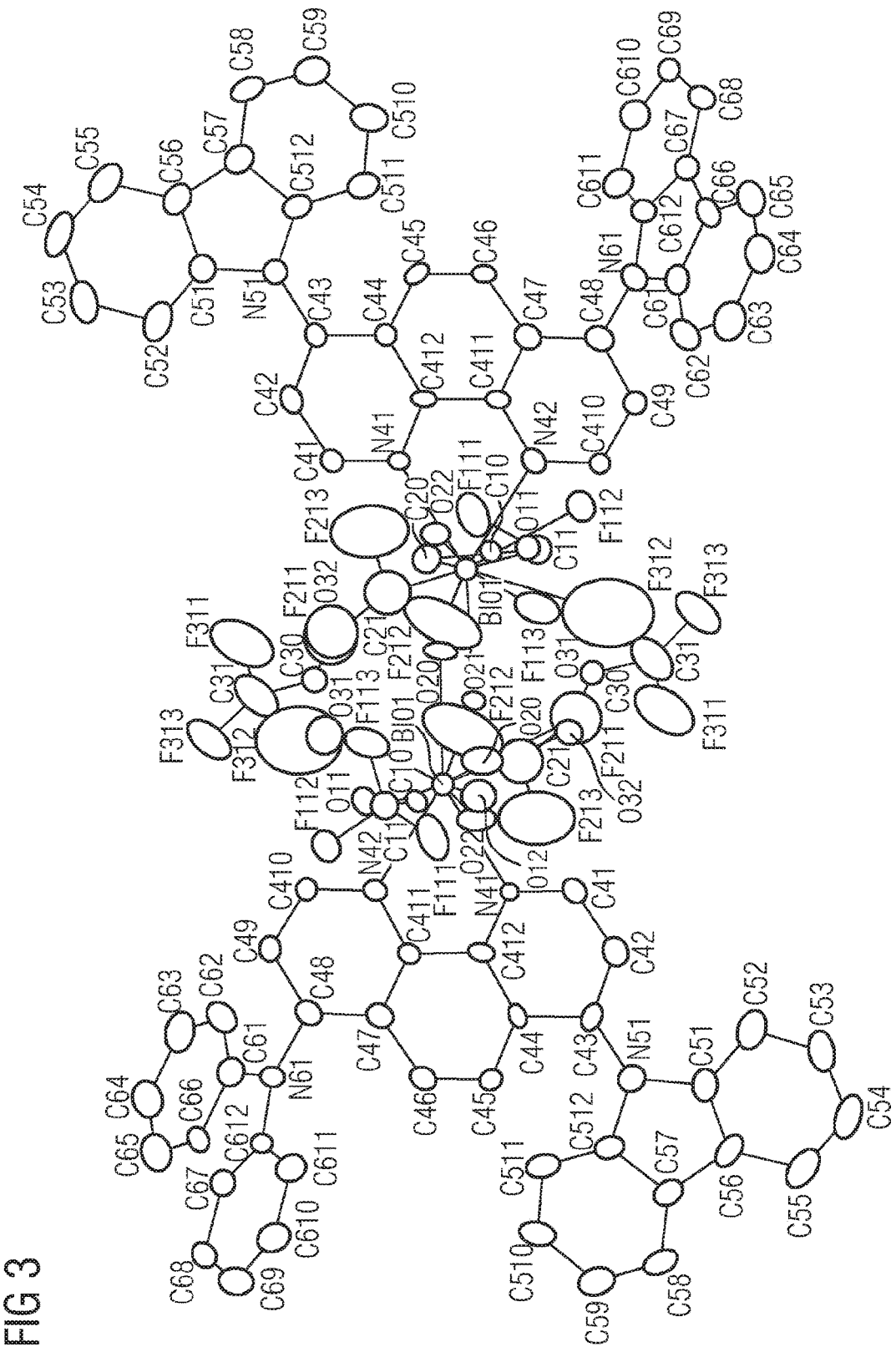
FIG. 3 shows a structure of a bi-nuclear phosphorescent emitter according to an embodiment having the composition hexakis-(µ-trifluoroacetate-k2O:O')bis[(4,7-di(9H-carbazol-9-yl)-1,10-phenanthroline-k2 N:N')bismuth(III)] (complex (2))
Figure 4:
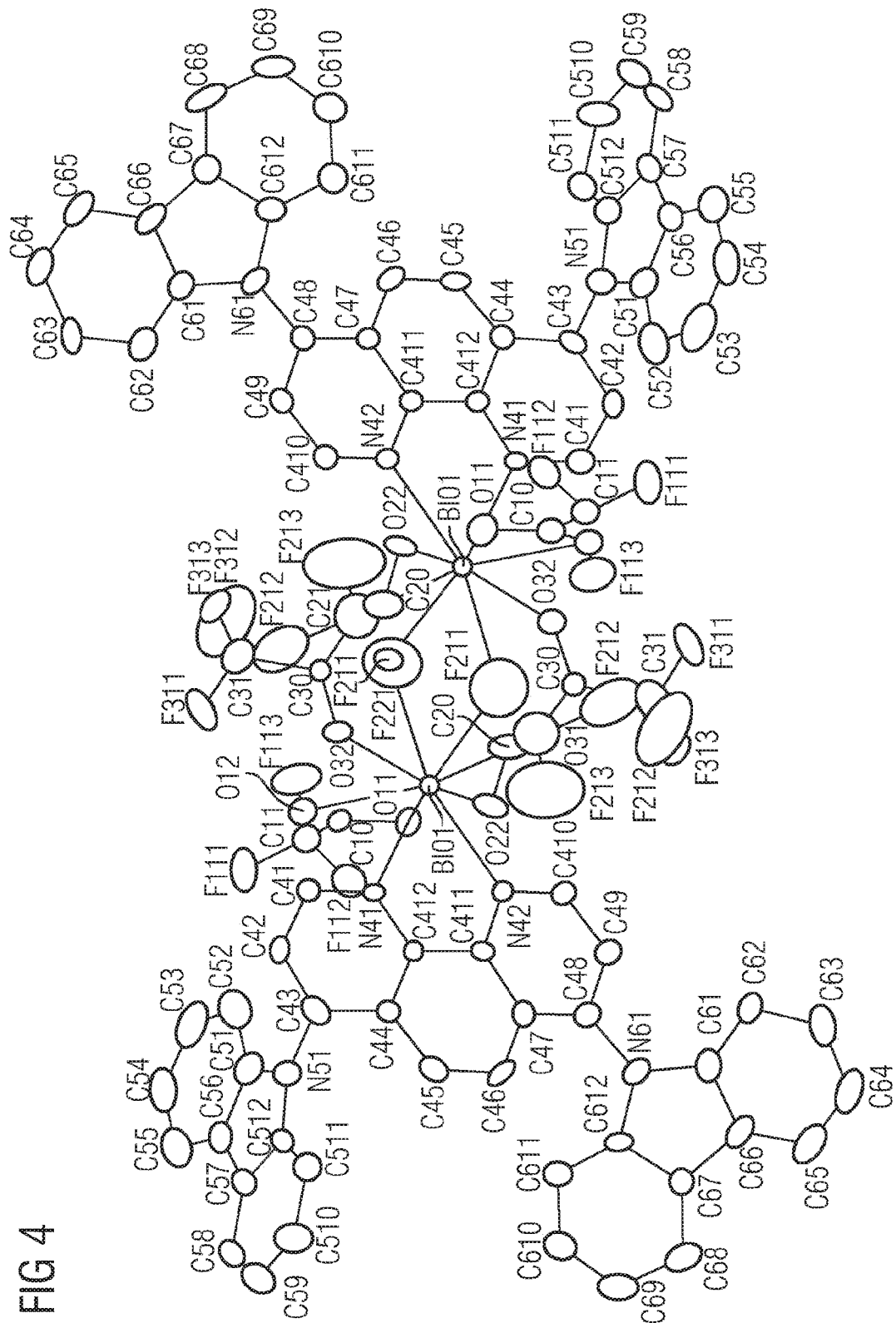
FIG. 4 shows an altered illustration of the structure of the complex 2, now with a view of the coordination of the terminal and bridging ligands on the bismuth atoms.

FIG. 3 and FIG. 4 show a further example of a bi-nuclear, phosphorescent emitter according to the invention. FIG. 3 shows in this case a bi-nuclear phosphorescent complex according to the invention, here hexakis-(μ-trifluoroacetate-k2O:O')bis[(4,7-di(9H-carbazol-9-yl)-1,10-phenanthroline-k2 N:N')bismuth(III)], having terminal and bridging ligands, and also two BUPH1 ligands as emitter ligands. FIG. 4 shows in this case the view of the BUPH1 ligands coordinated on the bismuth atoms. The crystal structure data for the complex (2) are reproduced in tables 4-6.

A second figure (Figure IIB) allows the view of the coordination of the terminal and bridging ligands on the bismuth atoms.

Production of Complex (2):
Crystallization:

In a Schlenk tube, bismuth(III) trifluoroacetate (21.5 mg; 0.0392 mmol) and BUPH1 (20 mg; 0.0392 mmol) are suspended in 10 ml toluene (molar ratio 1:1). The solution is stirred for approximately 30 minutes at 100° C. Crystals suitable for x-ray structural analysis are obtained by slow evaporation of the solvent at room temperature. The crystals obtained display upon irradiation using ultraviolet light, for example, of the wavelength 365 nm, a strong yellow-orange phosphorescence, which is not obtainable under the same conditions using pure BUPH1.

Production of the Emission Layers:

The complex 2-emitters according to the invention are deposited as a homogeneous layer having a thickness of 100 nm on a glass substrate by spin coating and then heated for 10 minutes at 100° C.; the concentration of the toluene solution is 25 mg/mL. The required rotational speed is dependent on the degree of dilution and the specific spin coater (100 nm at 1150 RPM). The layer displays phosphorescence after excitation using ultraviolet light.

TABLE 1

| (complex (1)): | | |
|---|---|---|
| Empirical formula | $C_{58}H_{24}BiCl_{12}F_{15}N_4O_6$ | |
| Formula weight | 1437.69 | |
| Temperature | 100(2) K | |
| Wavelength | 1.54178 Å | |
| Crystal system | Triclinic | |
| Space group | P-1 | |
| Dimensions of the unit cell | a = 12.5498(8) Å | α = 64.052(3)° |
| | b = 14.5308(9) Å | β = 84.778(4)° |
| | c = 16.3157(10) Å | γ = 72.409(4)° |
| Volume | 2547.3(3) Å$^3$ | |
| Z | 2 | |
| Density (calc.) | 1.874 Mg/m$^3$ | |
| Absorption coefficient | 8.793 mm$^{-1}$ | |
| F(000) | 1400 | |
| Crystal size | 0.080 × 0.040 × 0.020 mm$^3$ | |

TABLE 1-continued (complex (1)):

| | |
|---|---|
| Theta range of the data recording | 3.521 to 79.065°. |
| Index range | −13 <= h <= 15, −18 <= k <= 18, −19 <= l <= 20 |
| Number of reflections | 45220 |
| Independent reflections | 10444 [R(int) = 0.1061] |
| Completeness of theta = 67.679° | 98.7% |
| Refinement method | Full-matrix least-squares on $F^2$ |
| Data/restrictions/parameters | 10444/0/775 |
| Adaptation quality $F^2$ | 1.021 |
| Final R indices [I > 2sigma(I)] | R1 = 0.0742, wR2 = 0.1530 |
| R indices (total data) | R1 = 0.0954, wR2 = 0.1655 |
| Extinction coefficient | n/a |
| Greatest difference of peak and valley | 3.671 and −2.204 e · Å$^{-3}$ |

TABLE 2

(complex (1)):
Table of the atom coordinates and the equivalent isotropic displacement parameters (Å$^2$ × 10$^3$). U(eq) is defined as ⅓ of the absolute value of the track of the U$^{ij}$ tensor.

| | x | y | z | U(eq) |
|---|---|---|---|---|
| Bi(1) | 1003(1) | 3860(1) | 1144(1) | 28(1) |
| O(11) | 2818(6) | 2725(5) | 713(4) | 34(2) |
| O(12) | 1823(6) | 1919(5) | 1841(4) | 36(2) |
| C(10) | 2633(9) | 1924(8) | 1348(6) | 36(2) |
| C(11) | 3538(9) | 854(7) | 1588(7) | 36(2) |
| C(12) | 4224(9) | 388(9) | 2373(7) | 43(3) |
| F(12) | 4097(6) | 921(6) | 2887(4) | 53(2) |
| C(13) | 5011(10) | −594(10) | 2633(8) | 48(3) |
| F(13) | 5658(6) | −996(7) | 3399(5) | 71(2) |
| C(14) | 5174(11) | −1102(8) | 2078(9) | 51(3) |
| F(14) | 5973(6) | −2048(5) | 2307(6) | 66(2) |
| C(15) | 4539(10) | −643(9) | 1263(9) | 48(3) |
| F(15) | 4737(7) | −1140(6) | 721(6) | 71(2) |
| C(16) | 3730(10) | 338(9) | 1029(9) | 48(3) |
| F(16) | 3134(6) | 752(6) | 249(5) | 63(2) |
| O(21) | 1917(5) | 5183(5) | 105(4) | 29(1) |
| O(22) | 906(6) | 6364(5) | −1194(4) | 33(2) |
| C(20) | 1645(9) | 6043(7) | −591(7) | 31(2) |
| C(21) | 2254(8) | 6855(7) | −697(6) | 28(2) |
| C(22) | 2748(8) | 7349(7) | −1497(6) | 30(2) |
| F(22) | 2743(5) | 7118(5) | −2207(3) | 36(1) |
| C(23) | 3271(8) | 8096(8) | −1603(6) | 31(2) |
| F(23) | 3740(6) | 8587(5) | −2377(4) | 46(2) |
| C(24) | 3308(8) | 8372(8) | −895(7) | 38(2) |
| F(24) | 3816(6) | 9098(5) | −975(4) | 49(2) |
| C(25) | 2822(9) | 7897(8) | −86(7) | 36(2) |
| F(25) | 2851(6) | 8137(5) | 615(4) | 49(2) |
| C(26) | 2322(8) | 7123(8) | 6(6) | 29(2) |
| F(26) | 1849(5) | 6678(5) | 801(3) | 38(1) |
| O(31) | 445(6) | 5174(5) | 1699(4) | 34(2) |
| O(32) | −550(6) | 6127(6) | 389(5) | 42(2) |
| C(30) | −256(8) | 5986(8) | 1149(6) | 33(2) |
| C(31) | −784(8) | 6830(8) | 1477(6) | 33(2) |
| C(32) | −912(9) | 7915(8) | 928(6) | 33(2) |
| F(32) | −538(5) | 8231(5) | 81(4) | 43(2) |
| C(33) | −1368(9) | 8689(8) | 1241(8) | 40(2) |
| F(33) | −1433(6) | 9713(5) | 698(5) | 52(2) |
| C(34) | −1734(9) | 8384(9) | 2123(8) | 39(2) |
| F(34) | −2195(6) | 9126(5) | 2429(5) | 50(2) |
| C(35) | −1621(9) | 7324(9) | 2675(7) | 35(2) |
| F(35) | −1991(6) | 7040(5) | 3522(4) | 47(2) |
| C(36) | −1144(9) | 6563(8) | 2366(7) | 36(2) |
| F(36) | −1061(5) | 5546(5) | 2935(4) | 41(1) |
| N(41) | 2562(6) | 3546(6) | 2101(5) | 26(2) |
| N(42) | 591(7) | 3129(6) | 2798(5) | 30(2) |

TABLE 2-continued (complex (1)):
Table of the atom coordinates and the equivalent isotropic displacement parameters (Å$^2$ × 10$^3$). U(eq) is defined as ⅓ of the absolute value of the track of the U$^{ij}$ tensor.

| | x | y | z | U(eq) |
|---|---|---|---|---|
| C(41) | 3472(8) | 3805(7) | 1760(6) | 29(2) |
| C(42) | 4353(8) | 3663(8) | 2301(6) | 32(2) |
| C(43) | 4292(8) | 3210(8) | 3232(6) | 31(2) |
| C(44) | 3332(8) | 2914(7) | 3623(6) | 24(2) |
| C(45) | 3181(8) | 2472(8) | 4591(6) | 31(2) |
| C(46) | 2195(8) | 2291(7) | 4921(6) | 30(2) |
| C(47) | 1284(8) | 2534(7) | 4335(6) | 26(2) |
| C(48) | 213(8) | 2488(8) | 4632(6) | 30(2) |
| C(49) | −645(9) | 2757(8) | 4027(6) | 35(2) |
| C(410) | −378(8) | 3061(8) | 3101(6) | 33(2) |
| C(411) | 1426(7) | 2910(7) | 3384(6) | 24(2) |
| C(412) | 2461(8) | 3092(7) | 3032(6) | 27(2) |
| N(51) | 5146(7) | 3134(7) | 3792(5) | 35(2) |
| C(51) | 5318(10) | 4034(9) | 3815(7) | 40(2) |
| C(52) | 4779(10) | 5105(9) | 3330(8) | 43(3) |
| C(53) | 5102(11) | 5827(10) | 3493(8) | 52(3) |
| C(54) | 5965(12) | 5485(11) | 4145(9) | 56(3) |
| C(55) | 6466(11) | 4404(11) | 4661(9) | 55(3) |
| C(56) | 6153(9) | 3659(9) | 4496(7) | 40(2) |
| C(57) | 6488(8) | 2497(10) | 4902(7) | 40(3) |
| C(58) | 7262(10) | 1702(11) | 5595(7) | 52(3) |
| C(59) | 7409(10) | 649(11) | 5795(7) | 53(3) |
| C(510) | 6794(9) | 369(9) | 5319(7) | 43(3) |
| C(511) | 6016(9) | 1142(9) | 4626(7) | 37(2) |
| C(512) | 5871(8) | 2205(8) | 4434(6) | 34(2) |
| N(61) | −19(7) | 2207(6) | 5580(5) | 28(2) |
| C(61) | −568(8) | 2939(8) | 5918(6) | 30(2) |
| C(62) | −821(8) | 4044(8) | 5508(7) | 32(2) |
| C(63) | −1355(9) | 4590(8) | 6020(7) | 38(2) |
| C(64) | −1600(9) | 4063(9) | 6912(7) | 41(2) |
| C(65) | −1354(9) | 2942(8) | 7331(7) | 36(2) |
| C(66) | −825(8) | 2378(8) | 6832(6) | 33(2) |
| C(67) | −402(8) | 1257(8) | 7040(6) | 32(2) |
| C(68) | −395(9) | 314(8) | 7816(7) | 40(2) |
| C(69) | 87(10) | −646(9) | 7779(7) | 45(3) |
| C(610) | 566(11) | −701(8) | 6993(8) | 49(3) |
| C(611) | 580(9) | 211(8) | 6212(7) | 35(2) |
| C(612) | 83(8) | 1170(7) | 6249(6) | 32(2) |
| C(70) | 4029(14) | 3657(11) | 8956(9) | 69(4) |
| Cl(71) | 4697(3) | 4228(3) | 9420(2) | 66(1) |
| Cl(72) | 2934(3) | 4627(3) | 8160(3) | 71(1) |

TABLE 3

(complex (1)):
bond lengths [Å] and angles [°]
symmetry transformation to generate the equivalent atoms: #1
−x, −y + 1, −z

| | |
|---|---|
| Bi(1)—O(31) | 2.354(6) |
| Bi(1)—N(41) | 2.422(7) |
| Bi(1)—O(12) | 2.441(6) |
| Bi(1)—O(21) | 2.453(6) |
| Bi(1)—N(42) | 2.500(7) |
| Bi(1)—O(22) | 2.502(7) |
| Bi(1)—O(32) | 2.606(7) |
| Bi(1)—O(11) | 2.618(7) |
| Bi(1)—C(10) | 2.835(11) |
| O(11)—C(10) | 1.243(11) |
| O(12)—C(10) | 1.237(12) |
| C(10)—C(11) | 1.530(14) |
| C(11)—C(16) | 1.378(16) |
| C(11)—C(12) | 1.390(15) |
| C(12)—F(12) | 1.341(14) |
| C(12)—C(13) | 1.374(16) |
| C(13)—F(13) | 1.349(13) |
| C(13)—C(14) | 1.367(18) |
| C(14)—F(14) | 1.350(12) |
| C(14)—C(15) | 1.393(18) |
| C(15)—F(15) | 1.333(14) |

TABLE 3-continued (complex (1)):
bond lengths [Å] and angles [°]
symmetry transformation to generate the equivalent atoms: #1
−x, −y + 1, −z

| Bond | Value |
|---|---|
| C(15)—C(16) | 1.388(16) |
| C(16)—F(16) | 1.332(14) |
| O(21)—C(20) | 1.240(11) |
| O(22)—C(20) | 1.246(12) |
| O(22)—Bi(1) | 2.502(7) |
| C(20)—C(21) | 1.532(13) |
| C(21)—C(22) | 1.379(12) |
| C(21)—C(26) | 1.380(13) |
| C(22)—F(22) | 1.340(11) |
| C(22)—C(23) | 1.374(13) |
| C(23)—F(23) | 1.334(10) |
| C(23)—C(24) | 1.387(15) |
| C(24)—F(24) | 1.345(11) |
| C(24)—C(25) | 1.379(14) |
| C(25)—F(25) | 1.340(12) |
| C(25)—C(26) | 1.394(13) |
| C(26)—F(26) | 1.346(10) |
| O(31)—C(30) | 1.250(12) |
| O(32)—C(30) | 1.238(12) |
| O(32)—Bi(1) | 2.606(7) |
| C(30)—C(31) | 1.499(15) |
| C(31)—C(32) | 1.397(13) |
| C(31)—C(36) | 1.397(13) |
| C(32)—F(32) | 1.341(10) |
| C(32)—C(33) | 1.383(15) |
| C(33)—F(33) | 1.338(11) |
| C(33)—C(34) | 1.387(15) |
| C(34)—F(34) | 1.337(12) |
| C(34)—C(35) | 1.371(15) |
| C(35)—F(35) | 1.340(11) |
| C(35)—C(36) | 1.367(14) |
| C(36)—F(36) | 1.335(11) |
| N(41)—C(41) | 1.310(12) |
| N(41)—C(412) | 1.377(10) |
| N(42)—C(410) | 1.285(13) |
| N(42)—C(411) | 1.353(12) |
| C(41)—C(42) | 1.387(14) |
| C(42)—C(43) | 1.371(13) |
| C(43)—C(44) | 1.406(13) |
| C(43)—N(51) | 1.419(13) |
| C(44)—C(412) | 1.413(13) |
| C(44)—C(45) | 1.440(12) |
| C(45)—C(46) | 1.357(13) |
| C(46)—C(47) | 1.416(13) |
| C(47)—C(48) | 1.397(13) |
| C(47)—C(411) | 1.416(12) |
| C(48)—C(49) | 1.374(14) |
| C(48)—N(61) | 1.443(11) |
| C(49)—C(410) | 1.415(13) |
| C(411)—C(412) | 1.424(12) |
| O(31)—Bi(1)—N(41) | 73.9(3) |
| O(31)—Bi(1)—O(12) | 134.7(2) |
| N(41)—Bi(1)—O(12) | 75.7(2) |
| O(31)—Bi(1)—O(21) | 78.6(2) |
| N(41)—Bi(1)—O(21) | 78.2(2) |
| O(12)—Bi(1)—O(21) | 126.3(2) |
| O(31)—Bi(1)—N(42) | 66.8(2) |
| N(41)—Bi(1)—N(42) | 68.0(3) |
| O(12)—Bi(1)—N(42) | 71.0(2) |
| O(21)—Bi(1)—N(42) | 136.7(2) |
| O(31)—Bi(1)—O(22) | 94.3(2) |
| N(41)—Bi(1)—O(22) | 143.0(2) |
| O(12)—Bi(1)—O(22) | 90.2(2) |
| O(21)—Bi(1)—O(22) | 134.9(2) |
| N(42)—Bi(1)—O(22) | 75.1(2) |
| O(31)—Bi(1)—O(32) | 132.3(2) |
| N(41)—Bi(1)—O(32) | 141.7(2) |
| O(12)—Bi(1)—O(32) | 91.7(2) |
| O(21)—Bi(1)—O(32) | 80.9(2) |
| N(42)—Bi(1)—O(32) | 142.0(3) |
| O(22)—Bi(1)—O(32) | 71.3(2) |
| O(31)—Bi(1)—O(11) | 140.0(2) |
| N(41)—Bi(1)—O(11) | 71.3(2) |
| O(12)—Bi(1)—O(11) | 51.7(2) |
| O(21)—Bi(1)—O(11) | 75.6(2) |
| N(42)—Bi(1)—O(11) | 115.6(2) |
| O(22)—Bi(1)—O(11) | 125.4(2) |
| O(32)—Bi(1)—O(11) | 72.6(2) |
| O(31)—Bi(1)—C(10) | 144.2(3) |
| N(41)—Bi(1)—C(10) | 71.1(3) |
| O(12)—Bi(1)—C(10) | 25.8(2) |
| O(21)—Bi(1)—C(10) | 101.0(2) |
| N(42)—Bi(1)—C(10) | 93.1(3) |
| O(22)—Bi(1)—C(10) | 109.2(3) |
| O(32)—Bi(1)—C(10) | 81.8(3) |
| O(11)—Bi(1)—C(10) | 26.0(2) |
| C(10)—O(11)—Bi(1) | 86.8(6) |
| C(10)—O(12)—Bi(1) | 95.2(6) |
| O(12)—C(10)—O(11) | 126.2(10) |
| O(12)—C(10)—C(11) | 116.8(8) |
| O(11)—C(10)—C(11) | 116.8(9) |
| O(12)—C(10)—Bi(1) | 59.0(5) |
| O(11)—C(10)—Bi(1) | 67.2(6) |
| C(11)—C(10)—Bi(1) | 172.4(7) |
| C(16)—C(11)—C(12) | 117.7(10) |
| C(16)—C(11)—C(10) | 122.0(10) |
| C(12)—C(11)—C(10) | 120.2(10) |
| F(12)—C(12)—C(13) | 119.9(11) |
| F(12)—C(12)—C(11) | 118.2(10) |
| C(13)—C(12)—C(11) | 121.9(12) |
| F(13)—C(13)—C(14) | 121.7(11) |
| F(13)—C(13)—C(12) | 118.9(12) |
| C(14)—C(13)—C(12) | 119.2(11) |
| F(14)—C(14)—C(13) | 119.9(12) |
| F(14)—C(14)—C(15) | 119.3(12) |
| C(13)—C(14)—C(15) | 120.8(10) |
| F(15)—C(15)—C(16) | 121.7(12) |
| F(15)—C(15)—C(14) | 119.5(11) |
| C(16)—C(15)—C(14) | 118.8(11) |
| F(16)—C(16)—C(11) | 121.3(10) |
| F(16)—C(16)—C(15) | 117.3(11) |
| C(11)—C(16)—C(15) | 121.5(11) |
| C(20)—O(21)—Bi(1) | 137.0(6) |
| C(20)—O(22)—Bi(1) | 132.6(6) |
| O(21)—C(20)—O(22) | 129.1(9) |
| O(21)—C(20)—C(21) | 115.7(9) |
| O(22)—C(20)—C(21) | 115.1(8) |
| C(22)—C(21)—C(26) | 117.7(9) |
| C(22)—C(21)—C(20) | 121.5(9) |
| C(26)—C(21)—C(20) | 120.9(8) |
| F(22)—C(22)—C(23) | 116.8(8) |
| F(22)—C(22)—C(21) | 121.6(9) |
| C(23)—C(22)—C(21) | 121.6(9) |
| F(23)—C(23)—C(22) | 122.2(9) |
| F(23)—C(23)—C(24) | 118.0(8) |
| C(22)—C(23)—C(24) | 119.8(8) |
| F(24)—C(24)—C(25) | 118.5(10) |
| F(24)—C(24)—C(23) | 121.3(9) |
| C(25)—C(24)—C(23) | 120.2(9) |
| F(25)—C(25)—C(24) | 121.8(9) |
| F(25)—C(25)—C(26) | 119.7(9) |
| C(24)—C(25)—C(26) | 118.5(10) |
| F(26)—C(26)—C(21) | 120.6(8) |
| F(26)—C(26)—C(25) | 117.2(8) |
| C(21)—C(26)—C(25) | 122.2(8) |
| C(30)—O(31)—Bi(1) | 110.0(6) |
| C(30)—O(32)—Bi(1) | 171.8(7) |
| O(32)—C(30)—O(31) | 125.6(10) |
| O(32)—C(30)—C(31) | 119.2(9) |
| O(31)—C(30)—C(31) | 115.2(8) |
| C(32)—C(31)—C(36) | 116.4(9) |
| C(32)—C(31)—C(30) | 122.3(8) |
| C(36)—C(31)—C(30) | 121.3(9) |
| F(32)—C(32)—C(33) | 117.7(9) |
| F(32)—C(32)—C(31) | 120.0(9) |
| C(33)—C(32)—C(31) | 122.3(9) |
| F(33)—C(33)—C(32) | 119.8(10) |
| F(33)—C(33)—C(34) | 121.1(10) |
| C(32)—C(33)—C(34) | 119.0(9) |
| F(34)—C(34)—C(35) | 120.5(10) |

TABLE 3-continued (complex (1)):
bond lengths [Å] and angles [°]
symmetry transformation to generate the equivalent atoms: #1
−x, −y + 1, −z

| | |
|---|---|
| F(34)—C(34)—C(33) | 119.7(10) |
| C(35)—C(34)—C(33) | 119.9(10) |
| F(35)—C(35)—C(36) | 120.1(9) |
| F(35)—C(35)—C(34) | 119.3(9) |
| C(36)—C(35)—C(34) | 120.5(9) |
| F(36)—C(36)—C(35) | 117.7(9) |
| F(36)—C(36)—C(31) | 120.3(9) |
| C(35)—C(36)—C(31) | 121.9(10) |
| C(41)—N(41)—C(412) | 120.1(8) |
| C(41)—N(41)—Bi(1) | 122.2(6) |
| C(412)—N(41)—Bi(1) | 117.7(6) |
| C(410)—N(42)—C(411) | 119.4(8) |
| C(410)—N(42)—Bi(1) | 124.2(7) |
| C(411)—N(42)—Bi(1) | 116.0(6) |
| N(41)—C(41)—C(42) | 122.6(8) |
| C(43)—C(42)—C(41) | 119.4(9) |
| C(42)—C(43)—C(44) | 119.6(9) |
| C(42)—C(43)—N(51) | 120.0(9) |
| C(44)—C(43)—N(51) | 120.1(8) |
| C(43)—C(44)—C(412) | 118.1(8) |
| C(43)—C(44)—C(45) | 123.2(8) |
| C(412)—C(44)—C(45) | 118.7(8) |
| C(46)—C(45)—C(44) | 120.4(9) |
| C(45)—C(46)—C(47) | 121.8(8) |
| C(48)—C(47)—C(411) | 116.9(8) |
| C(48)—C(47)—C(46) | 123.7(8) |
| C(411)—C(47)—C(46) | 119.2(8) |
| C(49)—C(48)—C(47) | 121.0(8) |
| C(49)—C(48)—N(61) | 119.0(8) |
| C(47)—C(48)—N(61) | 119.9(8) |
| C(48)—C(49)—C(410) | 116.5(9) |
| N(42)—C(410)—C(49) | 124.4(9) |
| N(42)—C(411)—C(47) | 121.5(8) |
| N(42)—C(411)—C(412) | 119.1(8) |
| C(47)—C(411)—C(412) | 119.4(8) |
| N(41)—C(412)—C(44) | 120.2(8) |
| N(41)—C(412)—C(411) | 119.1(9) |
| C(44)—C(412)—C(411) | 120.3(8) |

TABLE 4

(complex (2)):

| | | |
|---|---|---|
| Empirical formula | C40H20Bi2F24N4O12 | |
| Formula weight | 1622.56 | |
| Temperature | 100(2) K | |
| Wavelength | 0.71073 Å | |
| Crystal system | Triclinic | |
| Space group | P-1 | |
| Dimensions of the unit cell | a = 12.3056(10) Å | α = 100.645(3)° |
| | b = 13.7641(11) Å | β = 92.984(3)° |
| | c = 15.1209(13) Å | γ = 92.233(3)° |
| Volume | 2510.5(4) Å³ | |
| Z | 2 | |
| Density (calc.) | 2.146 Mg/m³ | |
| Absorption coefficient | 7.152 mm⁻¹ | |
| F(000) | 1532 | |
| Crystal size | 0.05 × 0.06 × 0.3 mm³ | |
| Theta range of the data recording | 3.015 to 29.051°. | |
| Index range | −16 <= h <= 16, −18 <= k <= 18, −20 <= l <= 20 | |
| Number of reflections | 66726 | |
| Independent reflections | 13189 [R(int) = 0.0729] | |
| Completeness of theta = 67.679° | 99.3% | |
| Refinement method | Full-matrix least-squares on F² | |
| Data/restrictions/parameters | 13189/10/571 | |

TABLE 4-continued (complex (2)):

| | |
|---|---|
| Adaptation quality F² | 1.719 |
| Final R indices [I > 2sigma(I)] | R1 = 0.0757, wR2 = 0.2326 |
| R indices (overall data) | R1 = 0.0956, wR2 = 0.2391 |
| Extinction coefficient | n/a |
| Greatest difference peak and valley | 9.579 and −2.126 e · Å⁻³ |

TABLE 5

(complex (2)):
Table of the atom coordinates and the equivalent isotropic
displacement parameters (Å² × 10³). U(eq) is defined
as ⅓ of the absolute value of the track of the $U^{ij}$ tensor.

| | x | y | z | U(eq) |
|---|---|---|---|---|
| Bi(01) | 6611(1) | 563(1) | 465(1) | 15(1) |
| O(11) | 8082(6) | −446(6) | 69(5) | 28(2) |
| O(12) | 7940(6) | 576(6) | −937(5) | 26(2) |
| C(10) | 8349(8) | −116(7) | −633(6) | 18(2) |
| C(11) | 9292(9) | −674(8) | −1135(7) | 25(2) |
| F(111) | 9862(6) | −56(6) | −1553(5) | 44(2) |
| F(112) | 9973(5) | −1025(5) | −581(5) | 32(1) |
| F(113) | 8891(6) | −1439(6) | −1749(5) | 52(2) |
| O(21) | 5649(6) | −649(6) | −933(5) | 33(2) |
| O(22) | 4300(6) | −1663(6) | −1627(5) | 33(2) |
| C(20) | 5248(9) | −1355(10) | −1481(9) | 41(3) |
| C(21) | 6122(18) | −2045(16) | −1968(15) | 75(5) |
| F(211) | 6854(9) | −2311(10) | −1375(10) | 94(4) |
| F(212) | 6711(8) | −1355(14) | −2470(7) | 118(6) |
| F(213) | 5794(12) | −2763(12) | −2545(11) | 134(7) |
| O(31) | 6033(6) | −860(6) | 1111(5) | 28(2) |
| O(32) | 4425(6) | −1585(6) | 539(5) | 31(2) |
| C(30) | 5158(8) | −1341(8) | 1118(7) | 24(2) |
| C(31) | 4998(16) | −1640(20) | 2045(14) | 89(8) |
| F(311) | 4111(10) | −2073(14) | 2103(9) | 128(7) |
| F(312) | 4800(20) | −660(19) | 2627(9) | 187(10) |
| F(313) | 5867(9) | −1892(11) | 2425(8) | 101(5) |
| N(41) | 7725(6) | 2077(6) | 727(5) | 19(2) |
| N(42) | 7752(6) | 758(6) | 1859(5) | 19(2) |
| C(41) | 7720(8) | 2715(8) | 164(7) | 22(2) |
| C(42) | 8291(8) | 3606(8) | 350(7) | 24(2) |
| C(43) | 8852(8) | 3923(7) | 1173(7) | 23(2) |
| C(44) | 8838(8) | 3279(7) | 1818(7) | 20(2) |
| C(45) | 9289(8) | 3555(7) | 2719(7) | 23(2) |
| C(46) | 9305(8) | 2904(7) | 3293(6) | 23(2) |
| C(47) | 8839(8) | 1888(8) | 2993(6) | 20(2) |
| C(48) | 8896(8) | 1179(8) | 3532(7) | 25(2) |
| C(49) | 8358(8) | 253(8) | 3215(7) | 22(2) |
| C(410) | 7793(7) | 96(7) | 2391(7) | 20(2) |
| C(411) | 8284(7) | 1646(7) | 2153(6) | 18(2) |
| C(412) | 8269(7) | 2350(7) | 1546(6) | 18(2) |
| N(51) | 9438(8) | 4826(7) | 1367(6) | 28(2) |
| C(51) | 9076(10) | 5729(9) | 1145(8) | 33(2) |
| C(52) | 8007(12) | 5912(10) | 803(10) | 43(3) |
| C(53) | 7893(14) | 6862(10) | 657(9) | 48(4) |
| C(54) | 8708(14) | 7585(9) | 811(9) | 47(3) |
| C(55) | 9723(13) | 7404(9) | 1168(9) | 45(3) |
| C(56) | 9908(11) | 6441(8) | 1343(7) | 34(3) |
| C(57) | 10868(10) | 5985(8) | 1668(7) | 31(2) |
| C(58) | 11921(10) | 6333(10) | 1961(8) | 37(3) |
| C(59) | 12630(11) | 5701(11) | 2190(10) | 46(3) |
| C(510) | 12372(10) | 4694(10) | 2127(9) | 42(3) |
| C(511) | 11307(9) | 4331(9) | 1862(8) | 31(2) |
| C(512) | 10573(8) | 4997(8) | 1655(7) | 26(2) |
| N(61) | 9431(7) | 1351(7) | 4403(6) | 27(2) |
| C(61) | 8960(9) | 1116(8) | 5186(7) | 27(2) |
| C(62) | 7916(10) | 755(10) | 5268(8) | 34(3) |
| C(63) | 7660(11) | 609(10) | 6125(9) | 39(3) |
| C(64) | 8444(12) | 834(10) | 6857(8) | 42(3) |
| C(65) | 9483(11) | 1159(9) | 6744(8) | 36(3) |
| C(66) | 9728(10) | 1321(8) | 5908(7) | 29(2) |
| C(67) | 10719(9) | 1690(8) | 5569(7) | 26(2) |

TABLE 5-continued (complex (2)):
Table of the atom coordinates and the equivalent isotropic displacement parameters ($Å^2 \times 10^3$). U(eq) is defined as ⅓ of the absolute value of the track of the $U^{ij}$ tensor.

|  | x | y | z | U(eq) |
|---|---|---|---|---|
| C(68) | 11728(10) | 2018(9) | 5996(8) | 36(3) |
| C(69) | 12553(10) | 2300(10) | 5429(9) | 41(3) |
| C(610) | 12314(9) | 2221(9) | 4542(9) | 34(3) |
| C(611) | 11315(9) | 1942(8) | 4128(8) | 30(2) |
| C(612) | 10524(8) | 1666(7) | 4630(7) | 23(2) |

TABLE 6

(complex (2)):
Bond lengths [Å] and angles [°]
symmetry transformation to generate the equivalent atoms: #1
−x, −y + 1, −z

| Bi(01)—O(11) | 2.360(7) |
|---|---|
| Bi(01)—N(41) | 2.408(8) |
| Bi(01)—N(42) | 2.437(8) |
| Bi(01)—O(31) | 2.442(7) |
| Bi(01)—O(22) | 2.447(7) |
| Bi(01)—O(32) | 2.576(7) |
| Bi(01)—O(21) | 2.634(7) |
| Bi(01)—O(12) | 2.748(7) |
| Bi(01)—C(10) | 2.857(9) |
| O(11)—C(10) | 1.281(12) |
| O(12)—C(10) | 1.245(12) |
| C(10)—C(11) | 1.568(14) |
| C(11)—F(112) | 1.321(12) |
| C(11)—F(113) | 1.328(13) |
| C(11)—F(111) | 1.347(13) |
| O(21)—C(20) | 1.223(14) |
| O(22)—C(20) | 1.220(14) |
| O(22)—Bi(01) | 2.447(7) |
| C(20)—C(21) | 1.58(2) |
| C(21)—F(213) | 1.23(2) |
| C(21)—F(211) | 1.35(2) |
| C(21)—F(212) | 1.51(3) |
| O(31)—C(30) | 1.243(12) |
| O(32)—Bi(01) | 2.576(7) |
| C(30)—C(31) | 1.55(2) |
| C(31)—F(311) | 1.24(2) |
| C(31)—F(313) | 1.28(2) |
| C(31)—F(312) | 1.51(3) |
| N(41)—C(41) | 1.331(13) |
| N(41)—C(412) | 1.358(11) |
| N(42)—C(410) | 1.323(12) |
| N(42)—C(411) | 1.351(12) |
| C(41)—C(42) | 1.363(15) |
| C(42)—C(43) | 1.379(15) |
| C(43)—N(51) | 1.387(13) |
| C(43)—C(44) | 1.434(14) |
| C(44)—C(412) | 1.415(13) |
| C(44)—C(45) | 1.422(14) |
| C(45)—C(46) | 1.358(14) |
| C(46)—C(47) | 1.472(14) |
| C(47)—C(48) | 1.383(14) |
| C(47)—C(411) | 1.388(13) |
| C(48)—C(49) | 1.404(15) |
| C(48)—N(61) | 1.416(13) |
| C(49)—C(410) | 1.372(13) |
| C(411)—C(412) | 1.452(13) |
| O(11)—Bi(01)—N(41) | 93.9(3) |
| O(11)—Bi(01)—N(42) | 76.1(3) |
| N(41)—Bi(01)—N(42) | 68.2(3) |
| O(11)—Bi(01)—O(31) | 81.4(3) |
| N(41)—Bi(01)—O(31) | 144.6(2) |
| N(42)—Bi(01)—O(31) | 76.7(3) |
| O(11)—Bi(01)—O(22) | 148.7(3) |
| N(41)—Bi(01)—O(22) | 75.9(3) |
| N(42)—Bi(01)—O(22) | 72.6(3) |
| O(31)—Bi(01)—O(22) | 90.1(3) |
| O(11)—Bi(01)—O(32) | 126.9(3) |

TABLE 6-continued (complex (2)):
Bond lengths [Å] and angles [°]
symmetry transformation to generate the equivalent atoms: #1
−x, −y + 1, −z

| N(41)—Bi(01)—O(32) | 78.6(2) |
|---|---|
| N(42)—Bi(01)—O(32) | 141.3(3) |
| O(31)—Bi(01)—O(32) | 131.7(2) |
| O(22)—Bi(01)—O(32) | 80.7(3) |
| O(11)—Bi(01)—O(21) | 81.4(3) |
| N(41)—Bi(01)—O(21) | 137.0(3) |
| N(42)—Bi(01)—O(21) | 147.7(3) |
| O(31)—Bi(01)—O(21) | 77.2(3) |
| O(22)—Bi(01)—O(21) | 126.1(2) |
| O(32)—Bi(01)—O(21) | 71.1(3) |
| O(11)—Bi(01)—O(12) | 51.8(2) |
| N(41)—Bi(01)—O(12) | 70.2(3) |
| N(42)—Bi(01)—O(12) | 108.4(2) |
| O(31)—Bi(01)—O(12) | 127.4(3) |
| O(22)—Bi(01)—O(12) | 142.2(3) |
| O(32)—Bi(01)—O(12) | 76.8(2) |
| O(21)—Bi(01)—O(12) | 73.7(2) |
| O(11)—Bi(01)—C(10) | 26.3(3) |
| N(41)—Bi(01)—C(10) | 81.8(3) |
| N(42)—Bi(01)—C(10) | 93.2(3) |
| O(31)—Bi(01)—C(10) | 104.8(3) |
| O(22)—Bi(01)—C(10) | 156.7(3) |
| O(32)—Bi(01)—C(10) | 101.4(3) |
| O(21)—Bi(01)—C(10) | 75.4(3) |
| O(12)—Bi(01)—C(10) | 25.6(2) |
| C(10)—O(11)—Bi(01) | 99.1(6) |
| C(10)—O(12)—Bi(01) | 82.1(5) |
| O(12)—C(10)—O(11) | 126.9(9) |
| O(12)—C(10)—C(11) | 119.1(8) |
| O(11)—C(10)—C(11) | 114.0(8) |
| O(12)—C(10)—Bi(01) | 72.3(5) |
| O(11)—C(10)—Bi(01) | 54.6(5) |
| C(11)—C(10)—Bi(01) | 168.2(7) |
| F(112)—C(11)—F(113) | 107.1(9) |
| F(112)—C(11)—F(111) | 108.3(8) |
| F(113)—C(11)—F(111) | 108.5(9) |
| F(112)—C(11)—C(10) | 112.4(8) |
| F(113)—C(11)—C(10) | 110.6(8) |
| F(111)—C(11)—C(10) | 109.9(9) |
| C(20)—O(21)—Bi(01) | 167.0(10) |
| C(20)—O(22)—Bi(01) | 102.0(7) |
| O(22)—C(20)—O(21) | 129.9(11) |
| O(22)—C(20)—C(21) | 115.9(12) |
| O(21)—C(20)—C(21) | 113.6(12) |
| F(213)—C(21)—F(211) | 111.0(19) |
| F(213)—C(21)—F(212) | 105.4(18) |
| F(211)—C(21)—F(212) | 107.4(16) |
| F(213)—C(21)—C(20) | 118.2(17) |
| F(211)—C(21)—C(20) | 111.9(16) |
| F(212)—C(21)—C(20) | 101.8(15) |
| C(30)—O(31)—Bi(01) | 135.1(7) |
| C(30)—O(32)—Bi(01) | 130.7(7) |
| O(32)—C(30)—O(31) | 131.0(10) |
| O(32)—C(30)—C(31) | 116.8(10) |
| O(31)—C(30)—C(31) | 112.2(10) |
| F(311)—C(31)—F(313) | 120.7(17) |
| F(311)—C(31)—F(312) | 99(2) |
| F(313)—C(31)—F(312) | 102.2(19) |
| F(311)—C(31)—C(30) | 114.7(14) |
| F(313)—C(31)—C(30) | 114.2(16) |
| F(312)—C(31)—C(30) | 101.6(16) |
| C(41)—N(41)—C(412) | 118.5(8) |
| C(41)—N(41)—Bi(01) | 123.4(6) |
| C(412)—N(41)—Bi(01) | 117.5(6) |
| C(410)—N(42)—C(411) | 118.0(8) |
| C(410)—N(42)—Bi(01) | 124.3(6) |
| C(411)—N(42)—Bi(01) | 117.3(6) |
| N(41)—C(41)—C(42) | 122.9(9) |
| C(41)—C(42)—C(43) | 120.9(9) |
| C(42)—C(43)—N(51) | 121.3(9) |
| C(42)—C(43)—C(44) | 118.0(9) |
| N(51)—C(43)—C(44) | 120.7(9) |
| C(412)—C(44)—C(45) | 119.3(9) |
| C(412)—C(44)—C(43) | 116.9(9) |
| C(45)—C(44)—C(43) | 123.6(9) |

TABLE 6-continued (complex (2)):
Bond lengths [Å] and angles [°]
symmetry transformation to generate the equivalent atoms: #1
−x, −y + 1, −z

| | |
|---|---|
| C(46)—C(45)—C(44) | 121.6(9) |
| C(45)—C(46)—C(47) | 120.2(8) |
| C(48)—C(47)—C(411) | 119.0(9) |
| C(48)—C(47)—C(46) | 122.4(9) |
| C(411)—C(47)—C(46) | 118.6(9) |
| C(47)—C(48)—C(49) | 118.3(9) |
| C(47)—C(48)—N(61) | 123.6(10) |
| C(49)—C(48)—N(61) | 118.1(9) |
| C(410)—C(49)—C(48) | 118.6(9) |
| N(42)—C(410)—C(49) | 123.8(9) |
| N(42)—C(411)—C(47) | 122.4(9) |
| N(42)—C(411)—C(412) | 117.3(8) |
| C(47)—C(411)—C(412) | 120.4(8) |
| N(41)—C(412)—C(44) | 122.6(9) |
| N(41)—C(412)—C(411) | 118.3(8) |
| C(44)—C(412)—C(411) | 119.1(8) |

Although the invention was illustrated in greater detail and described by the preferred exemplary embodiment, the invention is thus not restricted by the disclosed examples and other variations can be derived therefrom by a person skilled in the art, without leaving the scope of protection of the invention.

What is claimed is:

1. A bi-nuclear phosphorescent emitter according to the following formula

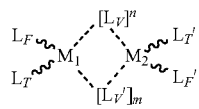

wherein the emitter comprises metal atoms $M_1$ and $M_2$, fluorescent emitter ligands $L_F$, $L_F'$, terminal ligands $L_T$, $L_T'$, and bridging ligands $L_V$, $L_V'$,
wherein each of $M_1$ and $M_2$ is an element selected from the group consisting of In, Tl, Sn, Pb, Sb, and Bi;
wherein each of $L_F$, $L_F'$ is selected from the group consisting of 4,7-di(9H-carbazol-9-yl)-1,10-phenanthroline, 2,6-bis(3-(9H-carbazol-9-yl)phenyl)pyridine, and 3,5-bis(3-(9H-carbazol-9-yl)phenyl)pyridine;
wherein each of $L_V$ and $L_V'$ is a compound selected from the group consisting of fluorinated and non-fluorinated, bi-dentate C2-C30 heteroalkyl and heteroaromatics;
wherein each of $L_T$ and $L_T'$ is a compound selected from the group consisting of fluorinated and non-fluorinated, mono-, bi-, or tri-dentate C2-C30 O—, S—, N—, heteroalkyl or heteroaromatics; and
wherein n is 1 or 2, and m is 1 or 2.

2. The emitter of claim 1, wherein:
$M_1$ and $M_2$ are selected independently of one another from the group consisting of Sb, As, and Bi; and
n, m=2.

3. The emitter of claim 1, wherein:
$M_1$ and $M_2$ are selected independently of one another from the group consisting of Pb and Sn.

4. The emitter of claim 1, wherein the emitter is a homonuclear emitter with $M_1=M_2=$Bi.

5. The emitter of claim 1, wherein distances between at least one metal atom and the ligands $L_V$, $L_V'$, $L_T$, $L_T'$ coordinated thereon are greater than or equal to 2.2 Å and less than or equal to 3.0 Å.

6. The emitter of claim 1, wherein at least one of $L_V$, $L_V'$ is selected from the group consisting of fluorinated and non-fluorinated C2-C30 O—, S—, N—, heteroalkyl, heterocycloalkyl, and heteroaromatics.

7. The emitter of claim 1, wherein the emitter corresponds to the following formula:

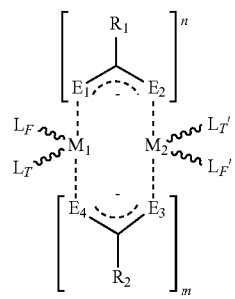

wherein $R_1$, $R_2$ are selected independently of one another from the group consisting of fluorinated and non-fluorinated C1-C30 alkyl, cycloalkyl, aryl, heteroalkyl, heterocycloalkyl, and heteroaryl; and
wherein $E_1$, $E_2$, $E_3$, $E_4$ are selected independently of one another from the group consisting of O, S, and NR, wherein R=H, D.

8. The emitter of claim 1, wherein at least one of the ligands $L_V$, $L_V'$ is selected from the group consisting of fluorinated and non-fluorinated aliphatic and aromatic C2-C30 carboxylates.

9. The emitter of claim 1, wherein at least one of the ligands $L_V$, $L_V'$ is selected from the group consisting of acetate, fluoroacetate, fluorobenzoate, fluoromethylbenzoate, fluoromethylfluorobenzoate, di-fluoromethyl-benzoate, and di-fluoromethyl-fluorobenzoate.

10. The emitter of claim 1, wherein at least one of the ligands $L_T$, $L_T'$ is selected from the group consisting of fluorinated or non-fluorinated aliphatic and aromatic C2-C30 alcoholates, carboxylates, benzoates, v acetylacetonates.

11. The emitter of claim 1, wherein at least one of the ligands $L_T$, $L_T'$ is selected from the group consisting of acetate, fluoroacetate, fluorobenzoate, fluoromethylbenzoate, fluoromethylfluorobenzoate, di-fluoromethyl-benzoate, and di-fluoromethyl-fluorobenzoate.

12. The emitter of claim 1, wherein each of the ligands $L_V$, $L_V'$, $L_T$, $L_T'$ is selected from the group comprising acetate, fluoroacetate, fluorobenzoate, fluoromethylbenzoate, fluoromethylfluorobenzoate, di-fluoromethyl-benzoate, and di-fluoromethyl-fluorobenzoate.

* * * * *